(12) United States Patent
Wilkie et al.

(10) Patent No.: US 12,227,434 B2
(45) Date of Patent: *Feb. 18, 2025

(54) HUMIC AND FULVIC BLACK WATER BASED BEVERAGE FOR HUMAN CONSUMPTION

(71) Applicants: Louise Wilkie, Calabasas, CA (US);
Jacqueline Wilkie, Calabasas, CA (US)

(72) Inventors: Louise Wilkie, Calabasas, CA (US);
Jacqueline Wilkie, Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/537,714

(22) Filed: Dec. 12, 2023

(65) Prior Publication Data
US 2024/0262716 A1    Aug. 8, 2024

Related U.S. Application Data

(63) Continuation of application No. 17/189,289, filed on Mar. 2, 2021, now Pat. No. 11,840,461, which is a
(Continued)

(51) Int. Cl.
*C02F 1/00*    (2023.01)
*A23L 2/72*    (2006.01)
(Continued)

(52) U.S. Cl.
CPC .............. *C02F 1/265* (2013.01); *A23L 2/72* (2013.01); *A23L 3/003* (2013.01); *A61L 2/0017* (2013.01);
(Continued)

(58) Field of Classification Search
CPC .. C02F 1/265; C02F 1/30; C02F 1/004; C02F 2103/08; C02F 2303/04; C02F 2101/14;
(Continued)

(56) References Cited

U.S. PATENT DOCUMENTS 2,380,800 A * 7/1945 Smith ................. C02F 1/281
                                                 252/189
5,626,881 A * 5/1997 Lown ................. A61K 35/10
                                                 514/960
(Continued)

FOREIGN PATENT DOCUMENTS

CN       1568827 A * 1/2005 ............... A23L 2/38
CN     104257843 A * 1/2015
(Continued)

OTHER PUBLICATIONS

English Translation of Patent Publication KR-100549662B1, published Feb. 7, 2006. (Year: 2006).*
(Continued)

*Primary Examiner* — Joseph W Drodge
(74) *Attorney, Agent, or Firm* — Edmond DeFrank

(57) ABSTRACT

The embodiments disclose a method including bottling alcoholic beverages with selected ingredients including alcohol neutral spirits, alcohol and whisky, beer, wine, ingredients to add flavors and nutritional additive ingredients to benefit the health of an alcoholic beverage drinker, wherein a selection of alcohols includes vodka, tequila, gin, rum, brandy and other alcoholic spirits, wherein a selection of ingredients to add flavors includes flavorings including fruit flavorings, an artificial sweetener, and natural sweetener, wherein a selection of nutritional additive ingredients includes vitamins, minerals, fulvic acid, humic acid, ulmic acid and a purified and sanitized black water with humic acid and fulvic acid molecules in a mixed solution, and wherein bottling includes a bottling electronic monitoring, at least one control network, at least one bottling quality control process and a bottling labeling and packaging process and devices.

14 Claims, 30 Drawing Sheets

Related U.S. Application Data continuation of application No. 16/377,210, filed on Apr. 7, 2019, now Pat. No. 10,934,511, which is a continuation-in-part of application No. 16/124,128, filed on Sep. 6, 2018, now Pat. No. 10,421,670, and a continuation-in-part of application No. 16/030,962, filed on Jul. 10, 2018, now Pat. No. 10,849,340.

(51) Int. Cl.

| | | |
|---|---|---|
| *A23L 3/00* | (2006.01) | |
| *A61L 2/00* | (2006.01) | |
| *B67C 7/00* | (2006.01) | |
| *C02F 1/26* | (2023.01) | |
| *C02F 1/30* | (2023.01) | |
| *C02F 101/14* | (2006.01) | |
| *C02F 103/00* | (2006.01) | |
| *C02F 103/02* | (2006.01) | |
| *C02F 103/08* | (2006.01) | |
| *C02F 103/10* | (2006.01) | |
| *C02F 103/26* | (2006.01) | |

(52) U.S. Cl.
CPC .......... *A61L 2/0023* (2013.01); *A61L 2/0047* (2013.01); *C02F 1/004* (2013.01); *C02F 1/30* (2013.01); *B67C 7/0073* (2013.01); *C02F 2101/14* (2013.01); *C02F 2103/007* (2013.01); *C02F 2103/02* (2013.01); *C02F 2103/08* (2013.01); *C02F 2103/10* (2013.01); *C02F 2103/26* (2013.01); *C02F 2209/02* (2013.01); *C02F 2209/06* (2013.01); *C02F 2303/04* (2013.01)

(58) Field of Classification Search
CPC .............. C02F 2209/06; C02F 2209/02; C02F 2103/26; C02F 2103/10; C02F 2103/007; C02F 1/008; C02F 1/02; C02F 1/32; C02F 1/68; C02F 1/685; C02F 1/686; C02F 1/78; C02F 9/00; C02F 2209/36; C02F 1/001; C02F 1/283; C02F 1/325; C02F 1/66; C02F 2101/12; C02F 2103/32; C02F 2303/16; C02F 2303/185; C02F 1/76; C02F 2103/02; C02F 2103/081; A23L 3/003; A23L 2/72; A23L 3/005; A23L 2/38; A23L 2/42; A23L 2/48; A23L 2/50; A23L 2/52; A23L 2/60; A23L 2/68; A23L 2/78; A23L 33/105; A23L 3/00; A23L 3/001; A23L 3/3409; A23L 3/3418; A23L 2/56; A23L 2/80; A23L 3/28; B67C 7/0073; B67C 3/007; B67C 3/0073; B67C 2003/228; A61K 33/00; A61K 9/0031; A61K 9/0095; A61K 9/02; A61K 9/025; A61K 9/08; A61K 31/185; A61K 31/19; A61K 36/00; A61K 36/899; A61K 9/1277; A61K 8/14; A61K 8/9794; A61K 31/05; A61K 31/122; A61K 31/353; A61K 31/726; A61K 9/0014; A61K 9/0056; A61K 9/006; A61K 9/127; A61K 36/185; A61K 36/886; C12G 3/04; C12G 3/08; C12G 3/085; C12C 12/00; C12C 12/002; A61L 2/0017; A61L 2/0023; A61L 2/0047; A61L 2/02; A61L 2/022; A61L 2/04; A61L 2/08; A61L 2/10; A61L 2/28; A23V 2002/00; G16B 50/30; G06Q 50/02; B01D 1/00; B01D 5/00; B01D 11/0207; B01D 11/028; B01D 29/00; B01D 29/0047; B01D 29/0052; B01D 29/0059; B01D 29/60; B01D 36/00; B01D 36/02; A61Q 19/08; A61Q 7/00; A61Q 11/00; A61Q 19/00
USPC .......... 210/85, 134, 143, 149, 175, 192, 335, 210/739, 764, 767, 774; 159/47.1; 426/388, 390, 392, 394, 419, 478, 479, 426/481, 514, 519, 590, 592, 615; 424/408, 422, 436, 725, 630, 641; 366/154.1, 162.1, 177.1, 197, 204; 99/275, 286, 287, 290, 537, 623; 604/285, 288; 206/528, 529; 514/966
See application file for complete search history.

(56) References Cited

U.S. PATENT DOCUMENTS

| | | | |
|---|---|---|---|
| 10,421,670 B1* | 9/2019 | Wilkie | C02F 1/30 |
| 10,849,340 B2* | 12/2020 | Wilkie | A23L 3/005 |
| 10,894,937 B2* | 1/2021 | Wilkie | A23L 2/58 |
| 10,918,690 B2* | 2/2021 | Wilkie | G06Q 50/02 |
| 10,934,511 B2* | 3/2021 | Wilkie | B67C 7/0073 |
| 11,497,230 B2* | 11/2022 | Wilkie | C02F 1/68 |
| 11,849,743 B2* | 12/2023 | Wilkie | A23L 3/005 |
| 2003/0150796 A1* | 8/2003 | Heinig, Jr. | C02F 1/505 |
| | | | 210/502.1 |
| 2007/0154614 A1* | 7/2007 | Sherwood | A23L 3/0155 |
| | | | 426/583 |
| 2008/0311253 A1* | 12/2008 | Mower | A23L 33/16 |
| | | | 426/72 |
| 2010/0113373 A1* | 5/2010 | Phillips | A61P 31/16 |
| | | | 435/375 |
| 2011/0171319 A1* | 7/2011 | Duoibes | A23L 33/16 |
| | | | 424/617 |
| 2012/0152755 A1* | 6/2012 | Martin | A61K 33/00 |
| | | | 205/335 |
| 2012/0183657 A1* | 7/2012 | Marina | B65D 81/3222 |
| | | | 215/6 |
| 2012/0207850 A1* | 8/2012 | Martin | A61K 9/0009 |
| | | | 514/724 |
| 2012/0213756 A1* | 8/2012 | Petralia | A61K 36/886 |
| | | | 424/94.1 |
| 2014/0010922 A1* | 1/2014 | Martin | A23L 2/38 |
| | | | 426/66 |
| 2015/0329225 A1* | 11/2015 | Moncayo, Jr. | A61L 2/07 |
| | | | 422/26 |
| 2015/0344399 A1* | 12/2015 | Martin | C10L 1/023 |
| | | | 562/488 |
| 2016/0008417 A1* | 1/2016 | Vandecar | A61K 36/48 |
| | | | 424/549 |
| 2016/0095877 A1* | 4/2016 | Martin | A23L 2/52 |
| | | | 514/724 |
| 2017/0129820 A1* | 5/2017 | Li | C05D 1/00 |
| 2018/0193403 A1* | 7/2018 | George | A61P 35/00 |

FOREIGN PATENT DOCUMENTS

| | | | | |
|---|---|---|---|---|
| CN | 106497821 A | * | 3/2017 | .......... A61K 9/0095 |
| CN | 107260842 A | * | 10/2017 | ......... A23V 2002/00 |
| KR | 100549662 B1 | * | 2/2006 | .............. A41B 9/02 |
| RU | 2423890 C1 | * | 7/2011 | .............. A23L 2/38 |
| TR | 201704453 A2 | * | 4/2018 | |

OTHER PUBLICATIONS

English Translation of Gladysh Patent Publication RU-2423890C1, published Jul. 20, 2011. (Year: 2011).*
Full English Translation of Patent Publication CN-104257843A, published Jan. 2015. (Year: 2015) (Year: 2015).*
Full English Translation of Patent Publication CN-106497821A, published Mar. 2017. (Year: 2017) (Year: 2017).*
Full English Translation of Patent Publication CN-107260842A, published Oct. 2017. (Year: 2017) (Year: 2017).*

(56) References Cited

OTHER PUBLICATIONS

Full English Translation of Murat Sevinc publication TR201704453A2, published Apr. 2018. (Year: 2018) (Year: 2018).*
English Translation of Patent Publication Cn 1568827-A, published Jan. 26, 2005. (Year: 2005).*

* cited by examiner

HUMIC AND FULVIC BLACK WATER BASED BEVERAGE FOR HUMAN CONSUMPTION

CROSS-REFERENCE TO RELATED APPLICATIONS

This Patent Application is a Continuation of and claims priority to United States Patent Application entitled: "HUMIC AND FULVIC BLACK WATER BASED BEVERAGE FOR HUMAN CONSUMPTION", U.S. Ser. No. 17/189,289, filed on Mar. 2, 2021 by Louise Wilkie, which is a Continuation of and claims priority to United States Patent Application entitled: "HUMIC AND FULVIC BLACK WATER BASED BEVERAGE FOR HUMAN CONSUMPTION", U.S. Ser. No. 16/377,210, filed on Apr. 7, 2019, which is a Continuation-in part of and claims priority to United States Patent Application entitled: "HUMIC AND FULVIC BLACK WATER BASED BEVERAGE FOR HUMAN CONSUMPTION", U.S. Ser. No. 16/030,962, filed on 0 Oct. 2018, and also a Continuation-in part of and claims priority to United States Patent Application entitled: "HUMIC AND FULVIC BLACK WATER BASED BEVERAGE FOR HUMAN CONSUMPTION", U.S. Ser. No. 16/124,128 filed on Sep. 6, 2018, and also a Continuation-in part of and claims priority to United States Patent Application entitled: "FULVIC ACID-HUMIC ACID COFFEE BREWER METHOD AND DEVICES", U.S. Ser. No. 16/751,557 filed on Sep. 1, 2020, and also a Continuation-in part of and claims priority to United States Patent Application entitled: "FULVIC ACID AND HUMIC ACID MIX FOR ALCOHOLIC BEVERAGES METHOD AND DEVICES", U.S. Ser. No. 16/751,562, filed on Jan. 24, 2020, this patent application is also a Continuation-in part of and claims priority to United States Patent Application entitled: "HUMIC AND FULVIC MINERAL EXTRACTION METHOD AND BEVERAGE FOR HUMAN CONSUMPTION", U.S. Ser. No. 17/985,998, filed on Nov. 14, 2022, which is a Continuation of and claims priority to United States Patent Application entitled: "HUMIC AND FULVIC MINERAL EXTRACTION METHOD AND BEVERAGE FOR HUMAN CONSUMPTION", U.S. Ser. No. 17/107,932, filed on Nov. 30, 2020, which is a Continuation of and claims priority to United States Patent Application entitled: "HUMIC AND FULVIC MINERAL EXTRACTION METHOD AND BEVERAGE FOR HUMAN CONSUMPTION", U.S. Ser. No. 16/030,962, filed on Jul. 10, 2018, this patent application is also a Continuation-in part of and claims priority to United States Patent Application entitled: "METHOD AND DEVICES FOR CELLULAR TRANSFER OF COMPOUNDS WITH AUGMENTED REALITY APPLICATION", U.S. Ser. No. 17/962,461 filed on Oct. 7, 2022, which is a Continuation of and claims priority to United States Patent Application entitled: "METHOD AND DEVICES FOR CELLULAR TRANSFER OF COMPOUNDS WITH AUGMENTED REALITY APPLICATION", U.S. Ser. No. 16/594,039, filed on Oct. 6, 2019, this patent application is also a Continuation-in part of and claims priority to United States Patent Application entitled: "NUTRITIONAL SUPPLEMENT BLACK SHOT MIXTURE METHOD AND APPARATUS", U.S. Ser. No. 17/940,926 filed on Sep. 8, 2022, which is a Continuation of and claims priority to United States Patent Application entitled: "CARBON HOOKS COMPOUND BONDING METHOD AND APPARATUS", U.S. Ser. No. 16/751,447 filed on Jan. 24, 2020, this patent application is also a Continuation-in part of and claims priority to United States Patent Application entitled: "FULVIC ACID AND HUMIC ACID NUTRACEUTICAL SUPPLEMENT SHOT AND METHOD", U.S. Ser. No. 17/151,658 filed on Jan. 18, 2021, wherein all the above U.S. Patent Applications are incorporated herein by reference.

BACKGROUND

Humic and fulvic acids are extracted using a number of chemical processes that add chemicals which are not suitable for human consumption or use. Those extracted humus sourced acids are used in fertilizers for agricultural use and in some cases added to animal feeds. Some of the chemicals used in the processes and some of the processes introduce chemicals borne in water that can produce chemical reactions or leave residual amounts that are known carcinogens. An extraction method to extract both humic and fulvic acids for human consumption and use should not include the use of those or similar types of chemicals and eliminate any added chemicals that could be present in any mixing water.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the embodiments.

GENERAL OVERVIEW

It should be noted that the descriptions that follow, for example, in terms of a black water beverage method and devices is described for illustrative purposes and the underlying system can apply to any number and multiple types of apparatuses and processes. In one embodiment of the present invention, the black water beverage method and devices for using at least one or more humate sources to extract humic and fulvic acids of one embodiment. The black water beverage method and devices includes at least one or more beverage product and includes black water, soft drinks and alcoholic beverages using the embodiments.

In one embodiment, the fulvic and humic water solution is used as a base for soda beverages, including cola and root beer. In another embodiment, the fulvic and humic water solution is used as a base for coffee and tea. In another embodiment, the black colored water is used as a base for carbonated water, distilled water, sparkling water, spring water and purified water. In another embodiment, the black colored water is used as a base for alcoholic beverages, such as for mixed alcoholic drinks.

Figure 1:
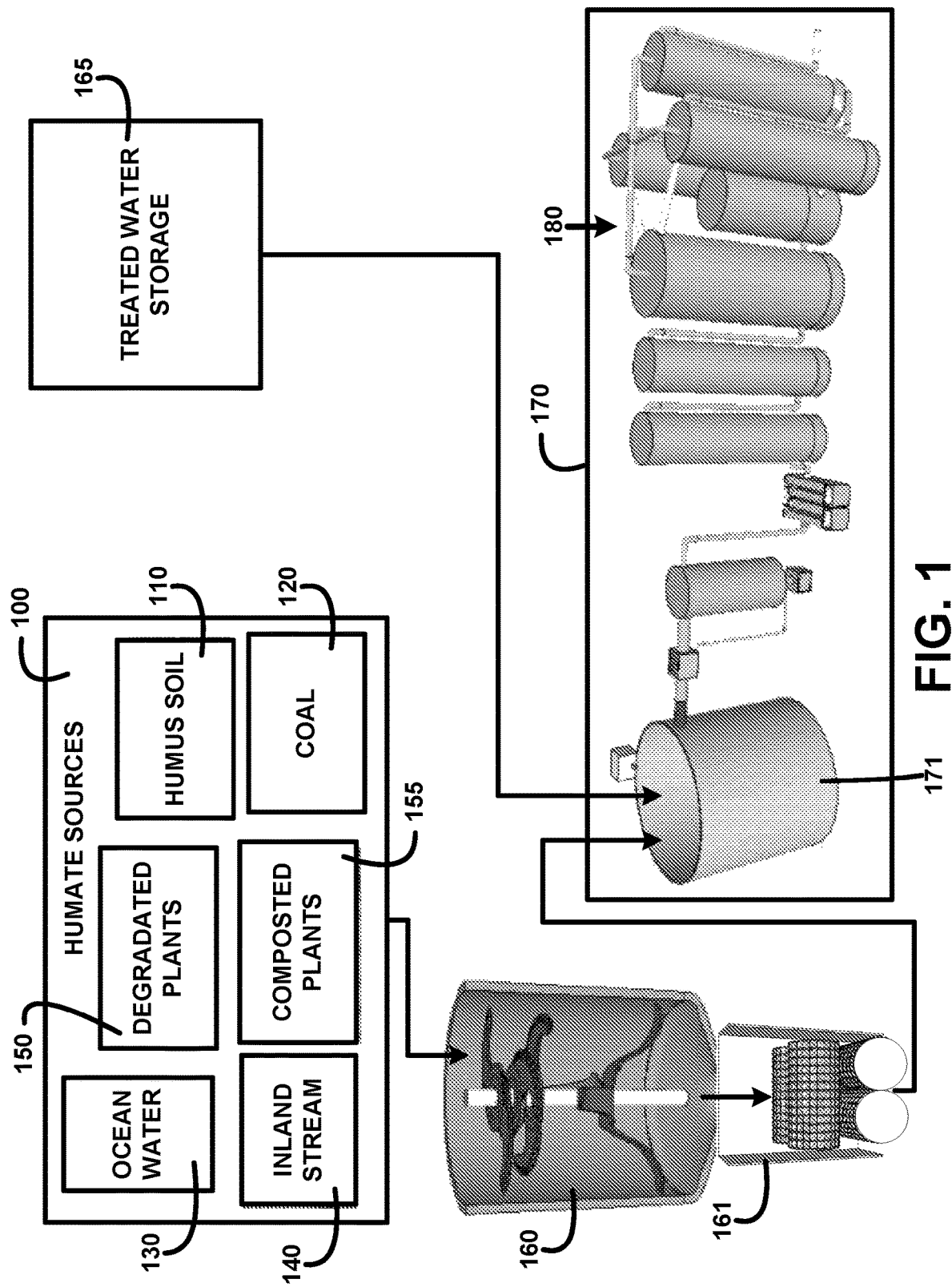
FIG. 1 shows a block diagram of an overview of black water humic and fulvic acids extraction for human consumption and use method and devices of one embodiment.

FIG. 1 shows a block diagram of an overview of black water humic and fulvic acids extraction for human consumption method and use and devices of one embodiment. FIG. 1 shows humate sources 100 including humus soil 110, coal 120, ocean water 130, inland stream 140, degradated plants 150 and composted plants 155. Treated water storage 165 contains a water source purified with various processes including filtration, ultrafiltration, purification, ultra-purification and sterilization that produce potable water. The treated water is mixed with at least one of the humate sources 100 that have been processed using a humate materials chopper 160 and chopped humate materials pulverizer 161 in a mixing tank 171.

The humate and treated water mixture filtration, dechlorination, defluoridation, sterilization, pH adjustment and temperature control devices and processes 170 is followed by humic and fulvic acid molecules separation and segregated storage suspended in purified water 180. The black water humic and fulvic acids extraction for human consumption and use method and devices processes and devices are controlled using digital processors, digital servers, digital computers, digital sensors, digital analyzers, digital valves, digital pumps, and other digitally controlled devices including wireless digital devices for automating individual process steps and operations. These processes produce humic and fulvic acids that are suitable for human consumption in for example a black colored water beverage, and other black colored water beverages including flavored beverages including a fruit flavored beverage, tea, coffee, soft drinks, alcoholic beverages, and products for human use including supplements, cosmetics, pharmaceuticals and food additives.

The humic and fulvic acids that are suitable for cosmetic products including for example skin moisturizers, perfumes, lipsticks, fingernail polishes, eye and facial makeup preparations, cleansing shampoos, permanent waves, hair colors and deodorants and other components used in cosmetic products. Hemp and medicinal legalized CBD and medicinal legalized cannabis are used in the solution for the human consumption beverages and the human use topical products for medicinal reasons. The humic and fulvic acids that are suitable for pharmacological products including for example fulvic sunscreen creams and lotions, fulvic first aid topical creams including fulvic topical agents to enhance healing of wounds infected with drug-resistant pathogens; and incorporating malacidins to attack and kill many types of super bugs, such as methicillin-resistant *Staphylococcus aureus* (MRSA) of one embodiment.

Composting a Humate Source:

Humus refers to decomposed organic matter. Humus is found on the forest floor where leaves and plant material decompose naturally. Humus can also result as a product of composting organic materials including vegetation. One humate source is degradated plants 150 of FIG. 1. Composting provides benefits in the supplying of composted plants 155 of FIG. 1 as a humate source as it is done in an organized and well managed process at virtually any location.

Decomposition of vegetative organic materials using composting is controlled to produce desired variants in a humate source. For example different vegetation selections are highly aromatic. On average 35% of the humic acid (HA) molecules are aromatic. Humate used for extracting humic and fulvic acids sourced from composting highly aromatic vegetation including flowers will retain the aromaticity of the selected vegetation. Products for human use and consumption including the aromatic humic acids ingredients can include the aromatic characteristics of the selected vegetation.

Selective composting can increase the production of humic and fulvic acids independently. For example, a composting environment that is acidic tends to produce plant debris with a greater percentage of fulvic acids. In a neutral and alkaline composting environment a large percentage of the organic matter is present in the form of humic acids and humin.

Organic matter is composed of minerals and trace elements required by plants. Different plants have varying amounts of certain minerals and trace elements. Composting of vegetation selected by the amounts of certain minerals and trace elements in the vegetation can result in the humic and fulvic acids extracted having greater concentrations of those certain minerals and trace elements for providing a desired purpose of one embodiment.

Fulvic and Humic Minerals:

Minerals and trace elements present in extracted humic and fulvic acids will vary by those present in the humate source materials. Some of the more common minerals present include iron (Fe), copper (Cu), zinc (Zn), magnesium (Mg), manganese (Mn), and calcium (Ca). Many scientific studies have shown that humic substances [humic acids (HAs) and fulvic acids (FAs)] present in the root zone of the organic vegetation of the humate material reduce the toxicity of metal cations.

Fulvic and Humic Minerals Supplements:

Supplements are a convenient way for a consumer to add additional vitamins, minerals and other beneficial elements to augment their dietary intake. Humic and fulvic acids in an aqueous solution is one preparation wherein the consumer can take a suggested dosage orally or put a suggested dosage into a familiar beverage or liquid containing food product for example a soup. Another preparation can include a powdered form wherein the humic and fulvic acids are mixed with for example a fruit for flavoring, the mixture liquefied and then dehydrated and pulverized into a powder. The pulverized powder is pressed into a tablet or filled into a suitable capsule container of one embodiment.

Fulvic and Humic Minerals Food Additives:

Food additives are prevalent in processed foods. Food additive can include for example essential vitamins to provide at least a portion of a recommended daily diet intake. Humic and fulvic acids in an aqueous solution is one preparation wherein a food digital processor can include a predetermined dosage into an ingredient mixture during processing for example a breakfast cereal, cookie batter, soup mixture or other processed food products. Another preparation can include a powdered form wherein an aqueous solution of humic and fulvic acids are mixed with for example other ingredients and dried or baked during the processing to form a powder or formed solid for example a baking mixture or a nutrient bar of one embodiment.

DETAILED DESCRIPTION

Figure 2:
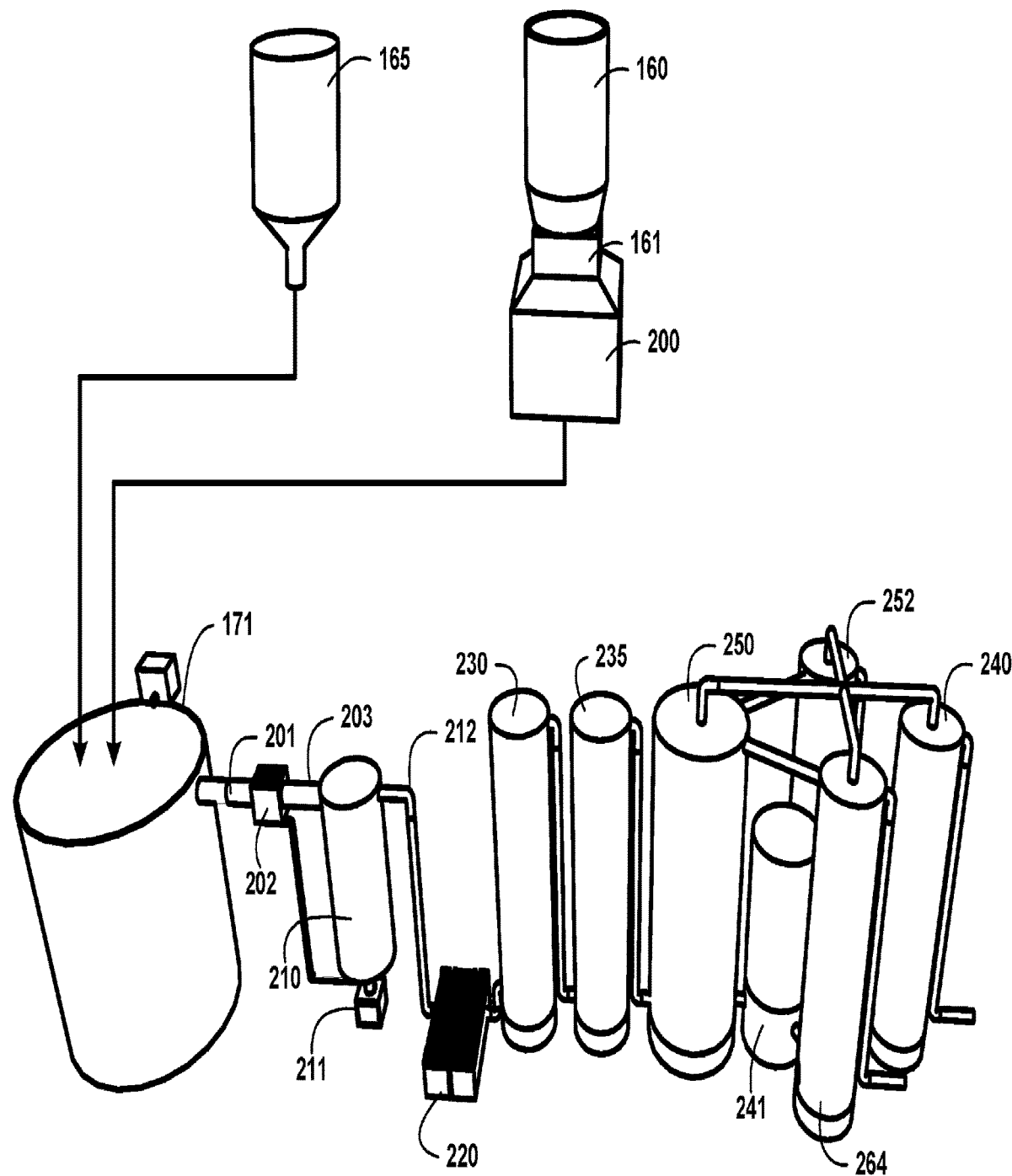
FIG. 2 shows for illustrative purposes only an example of black water humic and fulvic acids extraction for human consumption and use method and devices of one embodiment.

FIG. 2 shows for illustrative purposes only an example of black water humic and fulvic acids extraction for human consumption and use method and devices of one embodiment. FIG. 2 shows a process wherein at least one of the humate sources 100 of FIG. 1 is processed in the humate materials chopper 160 and chopped humate materials pulverizer 161 then collected in a chopped-pulverized humate material storage 200 and deposited in the mixing tank 171 with a quantity of treated water from the treated water storage 165. A humate-treated water mixture supply piping 201 conveys the mixture to a first stage humate-treated water mixture particulate filtration 202. The first stage humate-treated water mixture particulate filtration 202 can include ultrafiltration. Ultrafiltration involves the filtration of water through a semi-permeable membrane to remove suspended particles. Ultrafiltration is a physical filtration process typically used as a pretreatment method to separate solids from water used for industrial processes, such as food and beverage processing, semiconductor manufacturing, pharmaceutical production and power generation. A filtered humate-treated water mixture supply 203 is processed through a second stage humate-treated water mixture particulate filtration settling tank 210. The particulates filtered out of the mixture are accumulated in a particulate disposal container 211 of one embodiment.

UV light dechlorination 220 is performed on the mixture before it is processed to an adsorption defluoridation device 230 with granular activated carbon (GAC). The fluoride molecules adsorb to surfaces of the granular activated carbon (GAC). A fresh treated water storage tank 240 with a fresh treated water temperature control device and a pH control device 241 is used to supply additional water and control the desired PH level. The pH level is regulated to be greater than or equal than 8.5 and less than 10. A fresh treated water supply pipe 242 is used to convey treated water to a humic-fulvic acid separation chamber 250 with a bed of activated carbon material, a separation vacuum device, temperature regulating device and pH control device 241. The fulvic acid separation vacuum device and temperature regulating device process the separated fulvic acid molecules that have concentrated in the humic-fulvic acid separation chamber 250. The separation vacuum device uses a vacuum pressure to draw the concentrated fulvic acid molecules into a fulvic acid storage tank 252 with temperature and pH control device 241 of one embodiment.

A first humic acid separation chamber 260 with a humic acid separation vacuum device and temperature regulating device 263 in a second humic acid separation chamber 261 is used to draw separated humic acid molecules that have concentrated in the second humic acid separation chamber 262 into a humic acid storage tank 264 with temperature and pH control device 241. The segregated fulvic and humic acid molecules suspended in the treated water are stored for use in products of one embodiment.

Figure 3A:
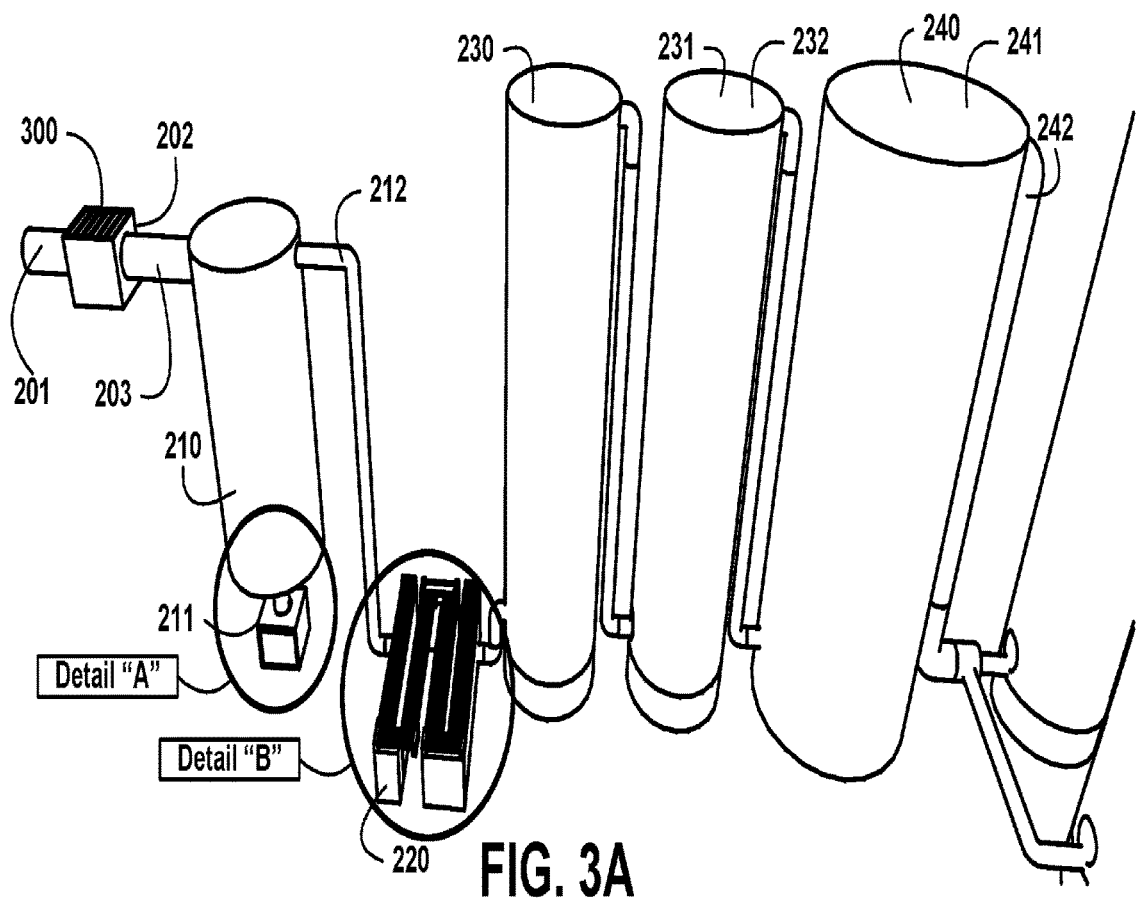
FIG. 3A shows for illustrative purposes only an example humic and fulvic acids extraction and separation of one embodiment.

Humic and Fulvic Acids Extraction and Separation:

FIG. 3A shows for illustrative purposes only an example of humic and fulvic acids extraction and separation of one embodiment. FIG. 3A shows the humate-treated water mixture supply piping 201 conveying the mixture to the first stage humate-treated water mixture particulate filtration 202. The humate-treated water mixture particulate filtration process 202 includes removable filter elements 300 including semi-permeable membrane filter elements. The filtered humate-treated water mixture supply 203 is processed through the second stage humate-treated water mixture particulate filtration settling tank 210. Particulates filtered out of the mixture are conveyed to the particulate waste disposal container 211 and second stage particulate disposal container 212 of one embodiment.

The UV light dechlorination 220 processes is followed by conveying the mixture to the adsorption defluoridation device 230. Chlorine and fluoride are found in water and found in humate sources through run-off of municipal water used domestically and by irrigation. These are harmful to humans at differing concentrations. After defluoridation settled ha-fa suspended mixture is stored in a settled ha-fa suspended mixture 232 settled ha-fa suspended mixture storage tank 231. Supplemental water 241 during the process is supplied from the fresh treated water storage tank 240 with the fresh treated water temperature control device through the fresh treated water supply pipe 242 of one embodiment.

Figure 3B:
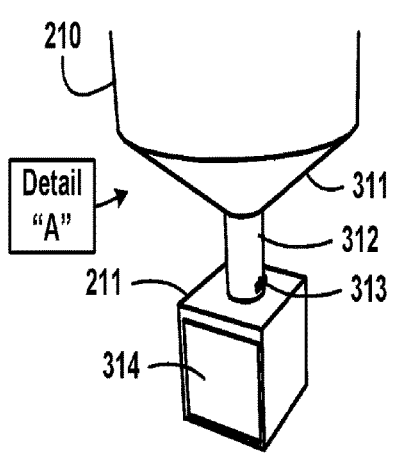
FIG. 3B shows for illustrative purposes only an example humic and fulvic acids extraction particulate waste separation of one embodiment.

Humic and Fulvic Acids Extraction Particulate Waste Separation:

FIG. 3B shows for illustrative purposes only an example of humic and fulvic acids extraction particulate waste separation of one embodiment. FIG. 3B shows a particulate waste accumulator funnel 311 used to accumulate the particulate waste at the particulate waste disposal discharge pipe 312 that includes a butterfly valve 313. The butterfly valve 313 is opened to pass the particulate waste to the particulate waste disposal container 211 from the particulate waste accumulator funnel 311. The particulate waste disposal container 211 includes a particulate waste water dehydrator 314 to dry the particulate waste for dry disposal and wet disposal of any liquid residue of one embodiment.

Figure 3C:
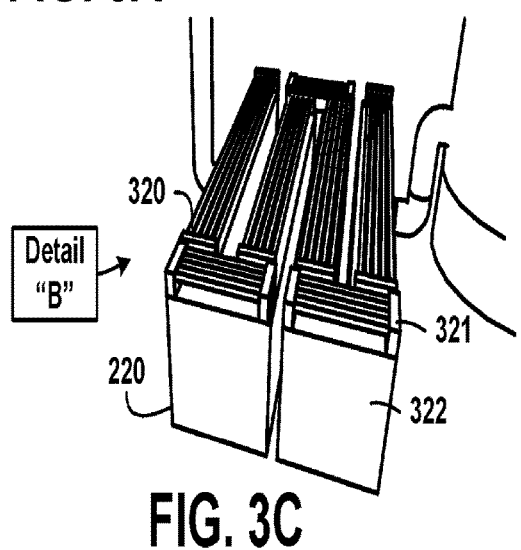
FIG. 3C shows for illustrative purposes only an example humic and fulvic acids extraction sterilization of one embodiment.

Humic and Fulvic Acids Extraction Sterilization:

FIG. 3C shows for illustrative purposes only an example of humic and fulvic acids extraction sterilization of one embodiment. FIG. 3C shows the UV light dechlorination 220 processor that includes UV light high intensity bulbs 320 and UV light ballast 321. The high intensity wave length UV light beams pass through the aqueous mixtures as it flows through a filtered humate-treated water mixture supply serpentine channel 322. The serpentine channel 322 is fabricated to allow a predetermined amount of UV light exposure to the aqueous mixture to kill microorganisms of one embodiment.

Figure 4:
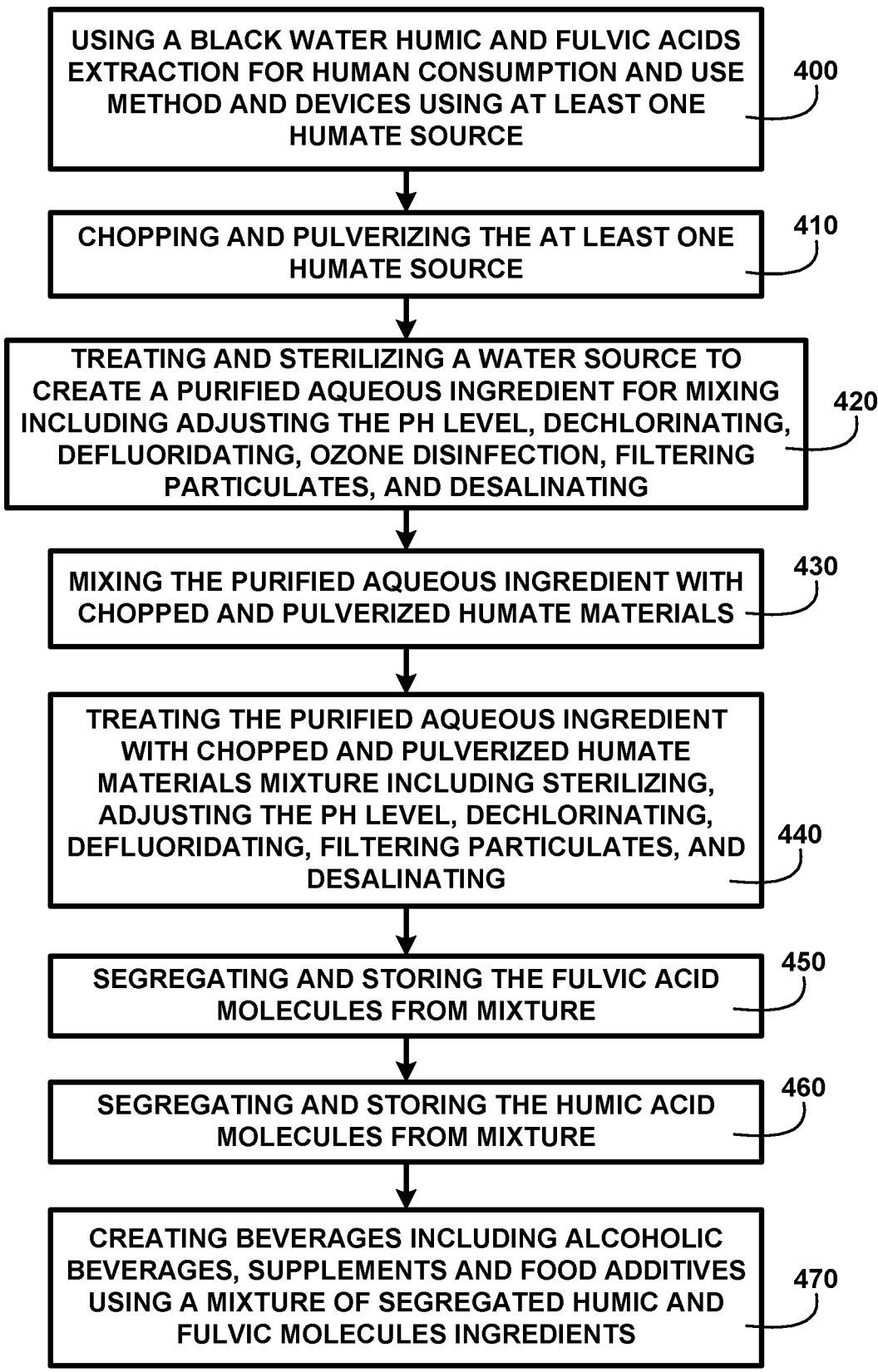
FIG. 4 shows a block diagram of an overview of extraction for human consumption and use processing of one embodiment.

Extraction for Human Consumption and Use Processing:

FIG. 4 shows a block diagram of an overview of extraction for human consumption and use processing of one embodiment. FIG. 4 shows using black water humic and fulvic acids extraction for human consumption and use method and devices using at least one humate source 400. A process is used for chopping and pulverizing the at least one humate source 410. Processing includes treating and sterilizing a water source to create a purified potable water source supply for mixing including adjusting the pH level, dechlorinating, defluoridating, filtering particulates, and desalinating 420. The processed humate source and treated and sterilized water are deposited into a mixing tank for mixing the purified aqueous ingredient with chopped and pulverized humate materials 430. The mixture ingredients are processed by treating the purified aqueous ingredient with chopped and pulverized humate materials mixture including sterilizing, adjusting the pH level, dechlorinating, defluoridating, filtering particulates, and desalinating 440. Processing continues for segregating and storing the fulvic acid molecules from mixture 450 and segregating and storing the humic acid molecules from mixture 460. The humic and fulvic acids extracted, segregated and suspended in an aqueous solution are used for creating a black colored water beverage, flavored beverages, soft drinks, alcoholic beverages, supplements and food additives using a mixture of segregated humic and fulvic molecules ingredients 470 of one embodiment.

The beverage is processed and treated with the extracted humic acid and fulvic acid molecules for creating a mixed solution, wherein the fulvic acid and humic acid molecules are sufficiently suspended within water molecules to create a black colored water.

Fulvic Cosmetic Products:

The humic and fulvic acids that are suitable for cosmetic products including for example skin moisturizers, perfumes, lipsticks, fingernail polishes, eye and facial makeup preparations, cleansing shampoos, permanent waves, hair colors and deodorants and other components used in cosmetic products. Fulvic cosmetic products can include pharmacological components for example incorporating malacidins and other antibiotic agents to enhance healing of wounds, skin irritants and infections of one embodiment.

Fulvic Pharmacological Products:

The humic and fulvic acids that are suitable for pharmacological products including for example fulvic sunscreen creams and lotions, fulvic first aid topical creams including fulvic topical agents to enhance healing of wounds infected with drug-resistant pathogens; and incorporating malacidins to attack and kill many types of super bugs, such as methicillin-resistant *Staphylococcus aureus* (MRSA) and other antibiotic agents to enhance healing of wounds, skin irritants and infections of one embodiment.

Figure 5:
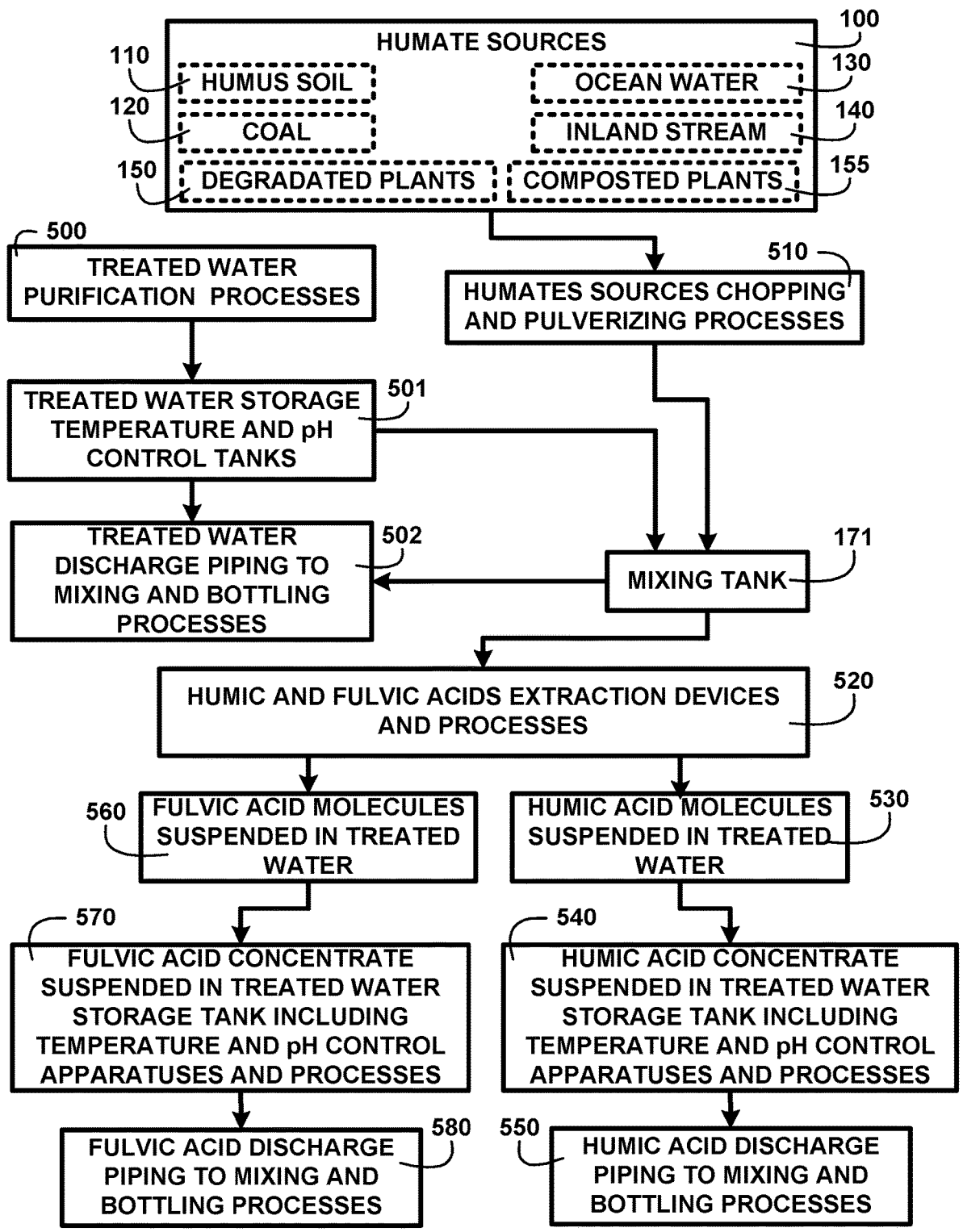
FIG. 5 shows a block diagram of an overview of humic and fulvic acids extraction devices and processes of one embodiment.

Humic and Fulvic Acids Extraction Devices and Processes:

FIG. 5 shows a block diagram of an overview of humic and fulvic acids extraction devices and processes of one embodiment. FIG. 5 shows humate sources 100 including humus soil 110, coal 120, ocean water 130, inland stream water 140, degraded plants 150 and composted plants 155. Treated water purification processes 500 are used to create potable water for human consumption and is stored in treated water storage temperature and pH control tanks 501. The treated water processes 500 can include creating oxygenated water using electrolysis and distilled water for human consumption and use. Treated water discharge piping to mixing and bottling processes 502 is used to deposit treated water to the mixing tank 171. Humate sources chopping and pulverizing processes 510 prepare the humate sources for deposition into the mixing tank 171 with the treated water.

Humic and fulvic acids extraction devices and processes 520 are used to separate humic acid molecules suspended in treated water 530 which are stored in humic acid concentrate suspended in treated water storage tank including temperature and pH control apparatuses and processes 540. The processed humic acid concentrate is conveyed through a humic acid discharge piping to mixing and bottling processes 550. Fulvic acid molecules suspended in treated water 560 are stored in fulvic acid concentrate suspended in treated water storage tank including temperature and pH control apparatuses and processes 570. The processed fulvic acid concentrate is conveyed through fulvic acid discharge piping to mixing and bottling processes 580.

The bottling processes include a filling control station where amounts of humic acid, fulvic acid and/or ulmic acid concentrates are added in predetermined quantities according to the beverage being bottled. For example ulmic acids are soluble in alcohol and may be added to the filling process for alcoholic beverages. Selective aromatic humic acids may be added to flavored or fruit beverages in a greater percentage than fulvic acids. Aromatic humic acids alone may be added to cosmetic products being bottled for example perfumes. The bottling processes include temperature regulating devices to assure the bottled mixtures do not exceed temperature thresholds both high and low established for the various types of beverages and to prevent clouding. The bottling processes also include pH level measurement devices to check and adjust the pH levels as the various beverage ingredients are added to prevent precipitation of the humic acid in an over acidic pH level of one embodiment.

Figure 6:
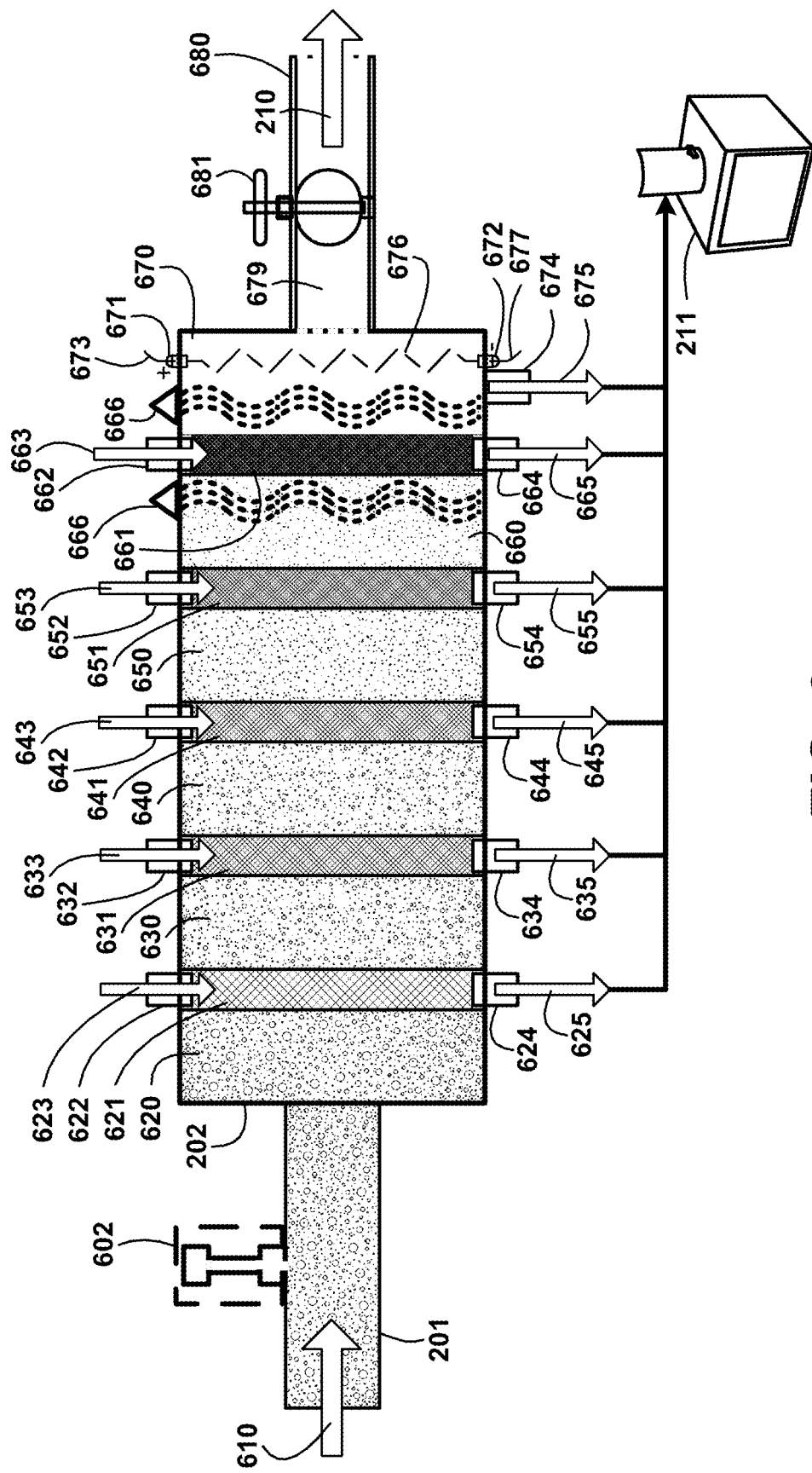
FIG. 6 shows for illustrative purposes only an example of first stage humate-treated water mixture particulate filtration of one embodiment.

First Stage Humate-Treated Water Mixture Particulate Filtration:

FIG. 6 shows for illustrative purposes only an example of first stage humate-treated water mixture particulate filtration of one embodiment. FIG. 6 shows the humate-treated water mixture supply piping 201 conveying a humate-treated water mixture supply 610 to a process. The humate-treated water mixture supply 610 is processed using pH sensors and PH level adjustment devices 602 to adjust the pH to a desired level. The pH level is adjusted to maintain a pH in which humic acid molecules are soluble in water. The first stage humate-treated water mixture particulate filtration 202 conveys an unfiltered humate-treated water mixture 620 through a first stage particulate filter 621. The first stage particulate filter 621 is a mesh at a predetermined size to block particulates of a size greater than the mesh openings. A first stage particulate filter treated water flush supply pipe 622 supplies first stage particulate filter flush treated water 623 to flush the blocked particulates off of the first stage particulate filter 621 to prevent clogging of mesh openings and allow the remaining fluid to pass through. The first stage particulate filter flush treated water 623 exits the first stage particulate filter 621 through a first stage particulate filter treated water flush discharge pipe 624 and first stage particulate filter flush treated water discharge 625 is conveyed to the particulate disposal container 211 of one embodiment.

A first stage particulate filtered humate-treated water mixture 630 is passed through a second stage particulate filter 631 mesh at a predetermined size to block particulates of a size greater than the mesh openings. A second stage particulate filter treated water flush supply pipe 632 conveys second stage particulate filter flush treated water 633 to clean the second stage particulate filter 631. The flush water exits through a second stage particulate filter treated water flush discharge pipe 634 wherein second stage particulate filter flush treated water discharge 635 is conveyed to the particulate disposal container 211 of one embodiment.

A second stage particulate filtered humate-treated water mixture 640 is passed through a third stage particulate filter 641 with a predetermined sized mesh to block particulates of a size greater than the mesh openings. A third stage particulate filter treated water flush supply pipe 642 conveys third stage particulate filter flush treated water 643 used to flush blocked particulates off of the third stage particulate filter 641. A third stage particulate filter treated water flush discharge pipe 644 conveys third stage particulate filter flush treated water discharge 645 to the particulate disposal container 211 of one embodiment.

A third stage particulate filtered humate-treated water mixture 650 passes through a fourth stage particulate filter 651 with a particulate blocking mesh of a predetermined size to block particulates larger than the mesh openings. Fourth stage particulate filter flush treated water 653 passes through a fourth stage particulate filter treated water flush supply pipe 652 to clean the fourth stage particulate filter 651. A fourth stage particulate filter treated water flush discharge pipe 654 passes fourth stage particulate filter flush treated water discharge 655 to the particulate disposal container 211 of one embodiment.

A fourth stage particulate filtered humate-treated water mixture 660 flows through a fifth stage particulate filter 661 with a mesh of a predetermined size to block particulates larger than the predetermined size. A fifth stage particulate filter treated water flush supply pipe 662 supplies fifth stage particulate filter flush treated water 663 to clean the fifth stage particulate filter 661 of blocked particulate which pass out of the filter through a fifth stage particulate filter treated water flush discharge pipe 664. Fifth stage particulate filter flush treated water discharge 665 is conveyed to the particulate disposal container 211. The fifth stage particulate filtered humate-treated water mixture 670 passes through piping to the next processes of one embodiment.

The fifth stage particulate filtered humate-treated water mixture 670 flows through a sixth stage particulate filter wherein UV light treatment devices 666 provide a treatment to kill bacteria and microorganisms and wherein a plurality of anodes 672 connected to a power circuit 677, not shown, and cathodes 671 connected to a power circuit 673, not shown, are energized to create an electrical charge 676 between an anode 672 and a corresponding cathode 671. The electrical charge 676 kills any bacteria and microorganisms, not shown, remaining in the fifth stage particulate filtered humate-treated water mixture 670.

Sixth stage particulate accumulation discharge 675 is conveyed to the particulate disposal container 211 through a sixth stage particulate accumulation discharge pipe 674. The sixth stage particulate filtered water 679 then flows out through a post filtration valve 681 and pipe 680 to the second stage humate-treated water mixture particulate filtration settling tank 210 of FIG. 2 of one embodiment.

Figure 7:
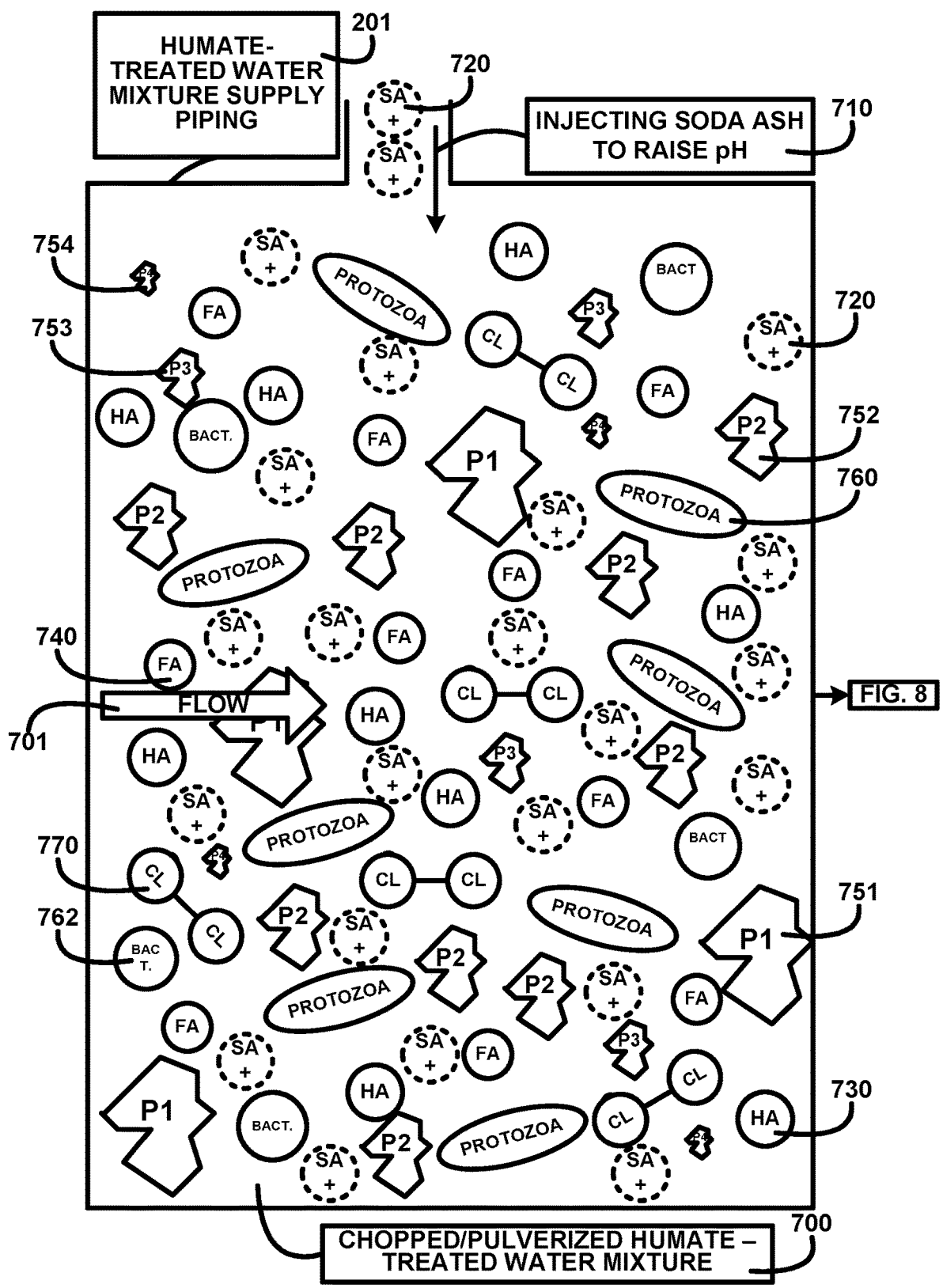
FIG. 7 shows for illustrative purposes only an example of chopped/pulverized humate-treated water mixture constituents of one embodiment.

Chopped/Pulverized Humate-Treated Water Mixture Constituents:

FIG. 7 shows for illustrative purposes only an example of chopped/pulverized humate-treated water mixture constituents of one embodiment. FIG. 7 shows chopped/pulverized humate-treated water mixture constituents 700 in the humate-treated water mixture supply piping 201. The mixture flow 701 is treated by injecting soda ash to raise pH 710 above the pH level of humic acid solubility. The chopped/pulverized humate-treated water mixture constituents 700 include s+ soda ash molecule 720, p2 particulate size 2 752, protozoa microorganism 760, p1 particulate size 1 751, p3 particulate size 3 753, p4 particulate size 4 754, ha humic acid molecule 730, bact. bacteria microorganism 762, cl chlorine molecule 770, fa fulvic acid molecule 740 of one embodiment. Descriptions of further processing are shown in FIG. 8.

Figure 8:
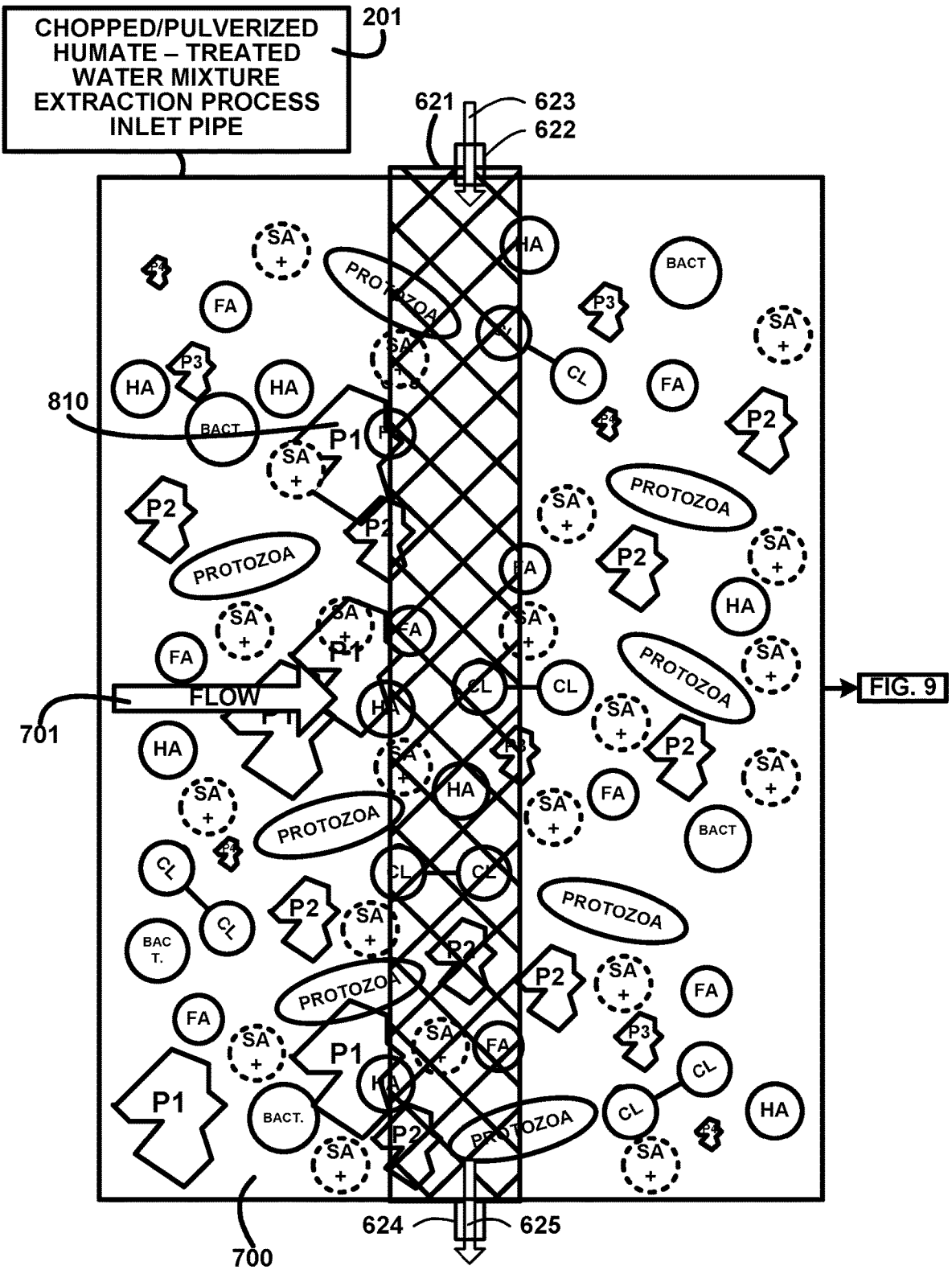
FIG. 8 shows for illustrative purposes only an example of first stage particulate filter of one embodiment.

First Stage Particulate Filter:

FIG. 8 shows for illustrative purposes only an example of first stage particulate filter of one embodiment. FIG. 8 shows continuing from FIG. 7 the humate-treated water mixture supply piping 201 conveys the mixture to the first stage particulate filter 621 flow 701 where p1 particulate size 1 are blocked 810 from the chopped/pulverized humate-treated water mixture 700. The first stage particulate filter treated water flush supply pipe 622 supplies first stage particulate filter flush treated water 623 to flush the blocked particulates off of the first stage particulate filter 621 to prevent clogging. The first stage particulate filter treated water flush discharge pipe 624 conveys the first stage particulate filter flush treated water discharge 625 of one embodiment. The description of the process continues on FIG. 9.

Figure 9:
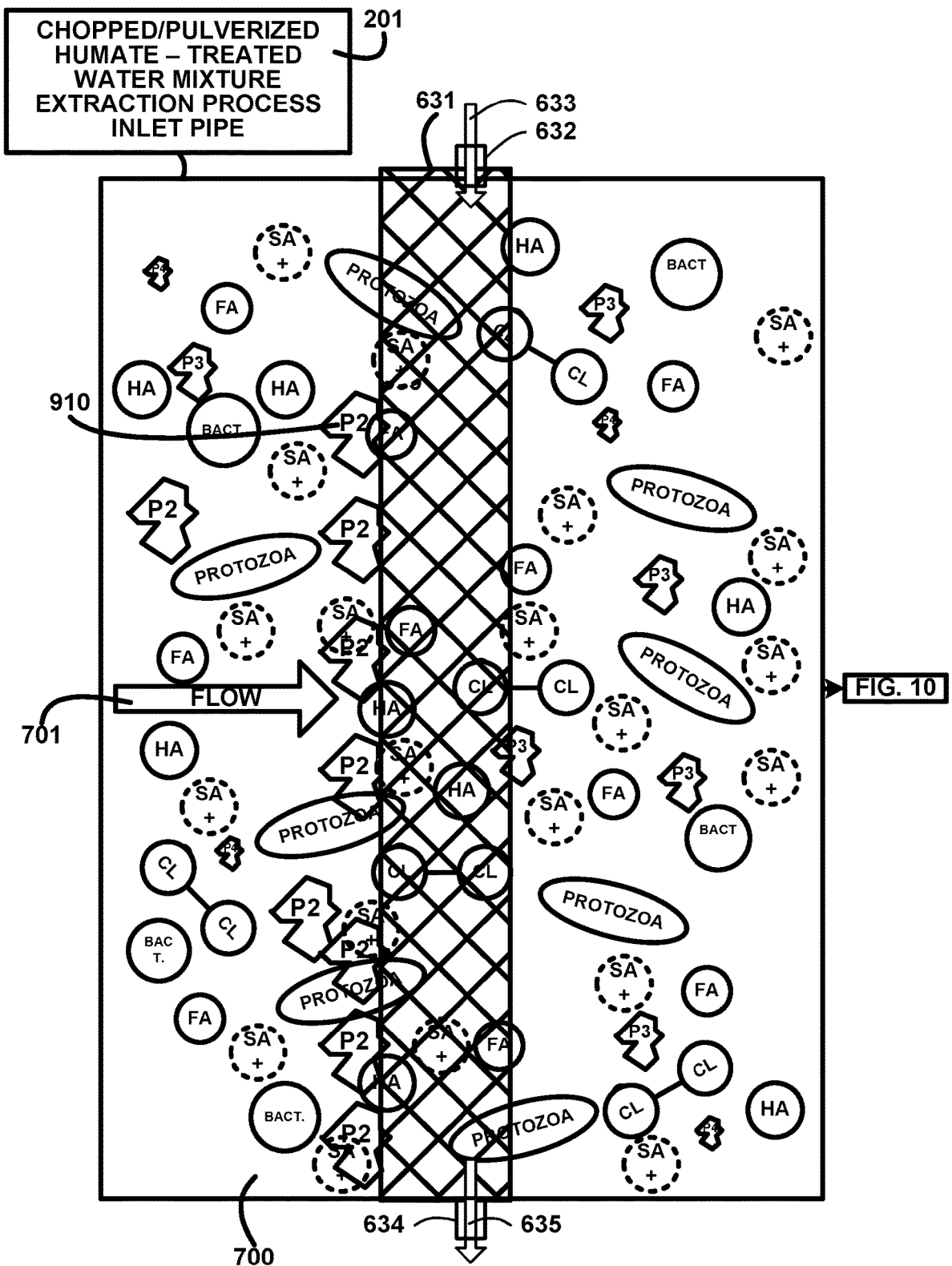
FIG. 9 shows for illustrative purposes only an example of second stage particulate filter of one embodiment.

Second Stage Particulate Filter:

FIG. 9 shows for illustrative purposes only an example of second stage particulate filter of one embodiment. FIG. 9 shows continuing from FIG. 8 the humate-treated water mixture supply piping 201 continue the flow 701 of the mixture through the second stage particulate filter 631 where p2 particulate size 2 are blocked 910 out of the chopped/pulverized humate-treated water mixture 700. The second stage particulate filter treated water flush supply pipe 632 conveys second stage particulate filter flush treated water 633 to clean the second stage particulate filter 631. The flush water exits through a second stage particulate filter treated water flush discharge pipe 634 wherein the second stage particulate filter flush treated water discharge 635 is conveyed of one embodiment. The description of the process continues on FIG. 10.

Figure 10:
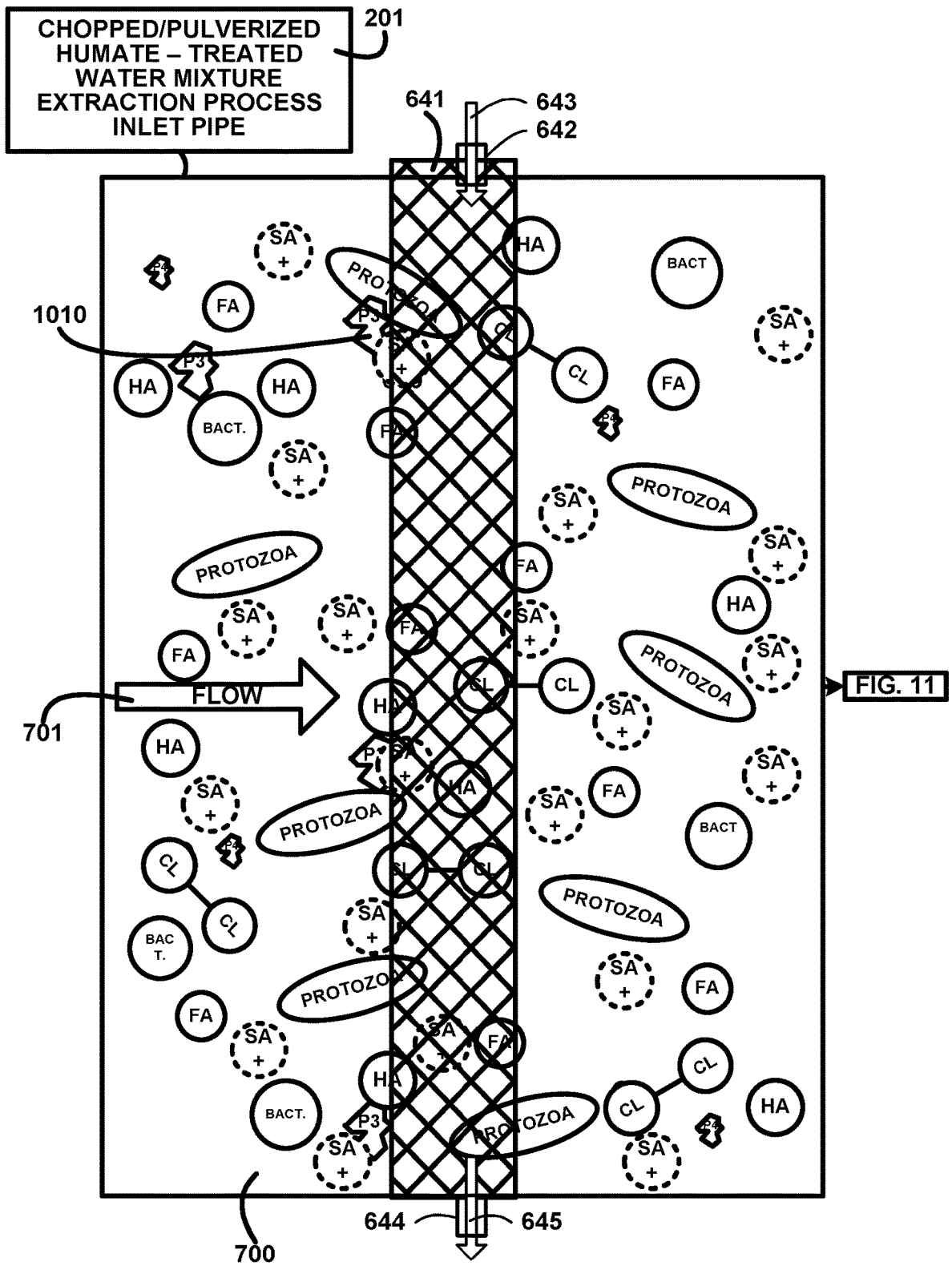
FIG. 10 shows for illustrative purposes only an example of third stage particulate filter of one embodiment.

Third Stage Particulate Filter:

FIG. 10 shows for illustrative purposes only an example of third stage particulate filter of one embodiment. FIG. 10 shows continuing from FIG. 9 the flow 701 through the humate-treated water mixture supply piping 201 through the third stage particulate filter 641 where p3 particulate size 3 are blocked 1010 out of the chopped/pulverized humate-treated water mixture 700. The third stage particulate filter treated water flush supply pipe 642 conveys third stage particulate filter flush treated water 643 used to flush blocked particulates off of the third stage particulate filter 641. The third stage particulate filter treated water flush discharge pipe 644 conveys third stage particulate filter flush treated water discharge 645 for discharge processing of one embodiment. The description of the process continues on FIG. 11.

Figure 11:
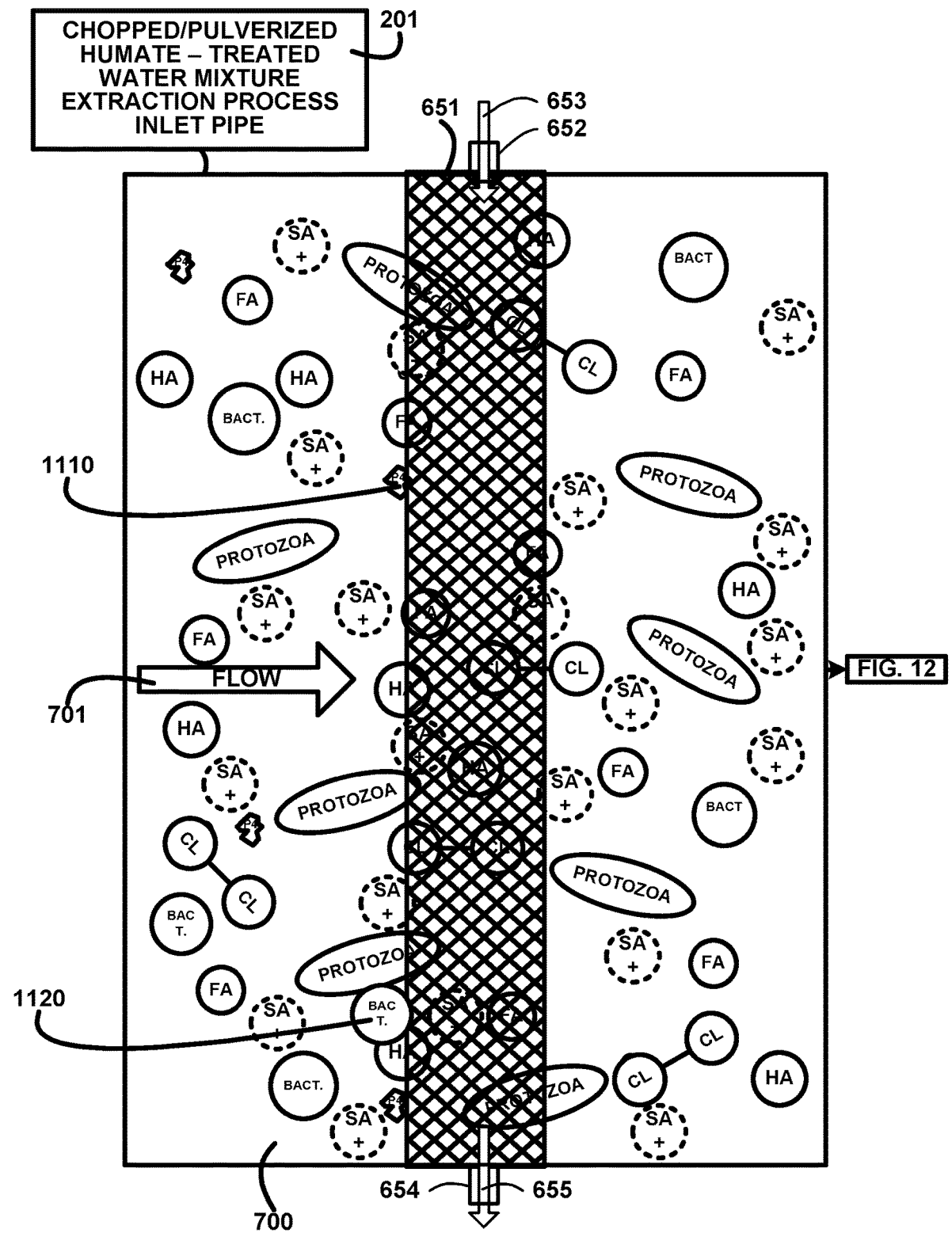
FIG. 11 shows for illustrative purposes only an example of fourth stage particulate filter of one embodiment.

Fourth Stage Particulate Filter:

FIG. 11 shows for illustrative purposes only an example of fourth stage particulate filter of one embodiment. FIG. 11 shows continuing from FIG. 10 humate-treated water mixture supply piping 201 continuing the flow 701 to pass through fourth stage particulate filter 651 where p4 particulate size 4 are blocked 1110 and bact. bacteria microorganism are blocked 1120 out of the chopped/pulverized humate-treated water mixture 700. The fourth stage particulate filter flush treated water 653 passes through a fourth stage particulate filter treated water flush supply pipe 652 to clean the fourth stage particulate filter 651. The fourth stage particulate filter treated water flush discharge pipe 654 passes fourth stage particulate filter flush treated water discharge 655 of one embodiment. The description of the process continues on FIG. 12.

Figure 12:
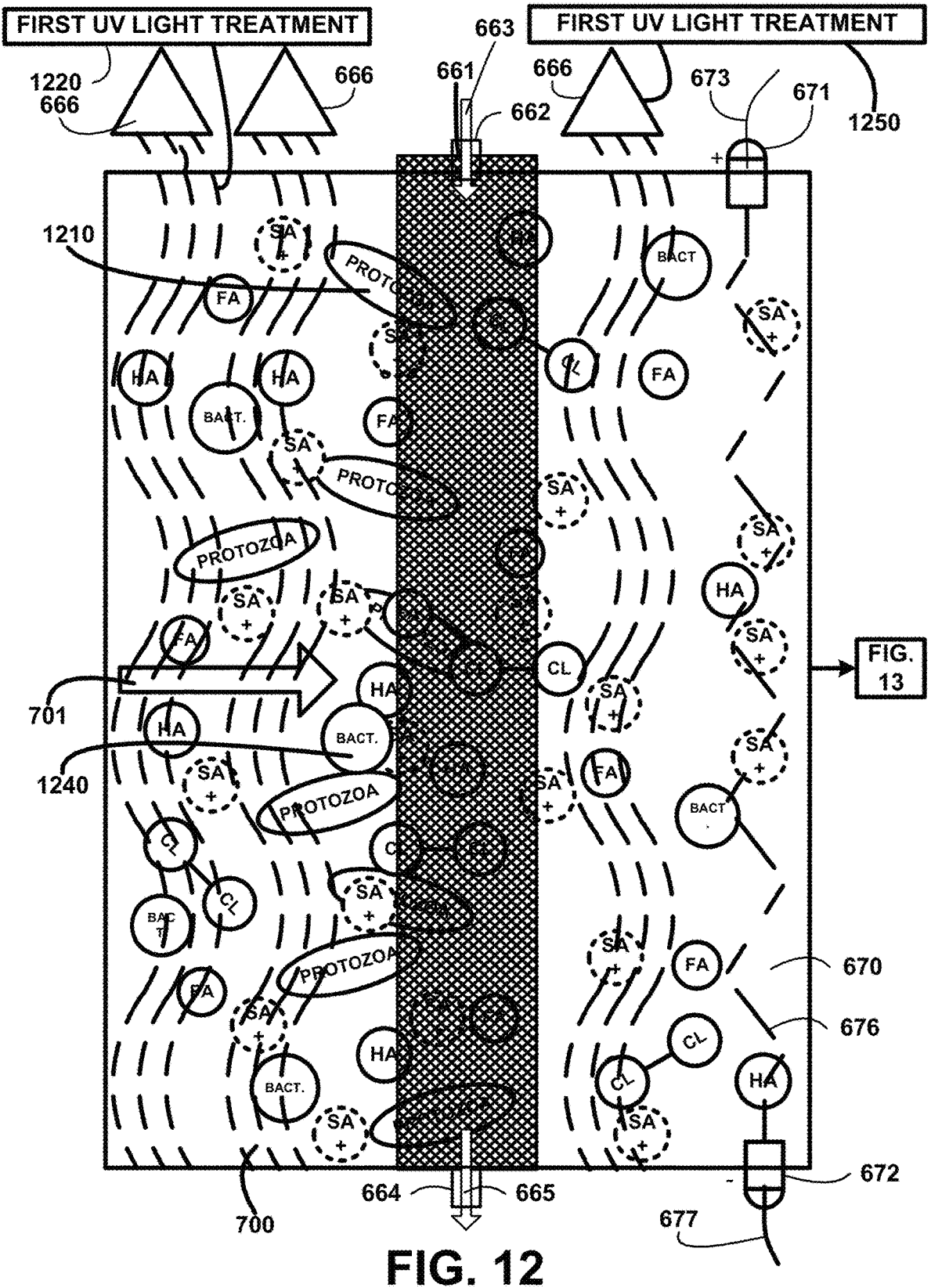
FIG. 12 shows for illustrative purposes only an example of fifth stage particulate filter of one embodiment.

Fifth Stage Particulate Filter:

FIG. 12 shows for illustrative purposes only an example of fifth stage particulate filter of one embodiment. FIG. 12 shows continuing from FIG. 11 the flow 701 passing through the humate-treated water mixture supply piping 201 where UV light treatment devices 666 provide a first UV light treatment process sterilization 1220 then flows to and through the fifth stage particulate filter 661. The mixture is also processed using a continuation of the first UV light treatment process sterilization 1250 after passing through the fifth stage particulate filter 661 where bact. bacteria microorganism and protozoa are killed in the chopped/pulverized humate-treated water mixture 700.

The first UV light treatment process sterilization 1220 includes UV light treatment devices 666 to produce beams of the UV light for penetrating the mixture and killing the bacteria microorganisms and protozoa microorganisms. The plurality of anodes 672 and cathodes 671 are energized to create an electrical charge 676 between an anode 672 and a corresponding cathode 671. The electrical charge 676 kills any bacteria and microorganisms, not shown, remaining in the fifth stage particulate filtered humate-treated water mixture 670 of one embodiment. The description of the process continues on FIG. 13.

Figure 13:
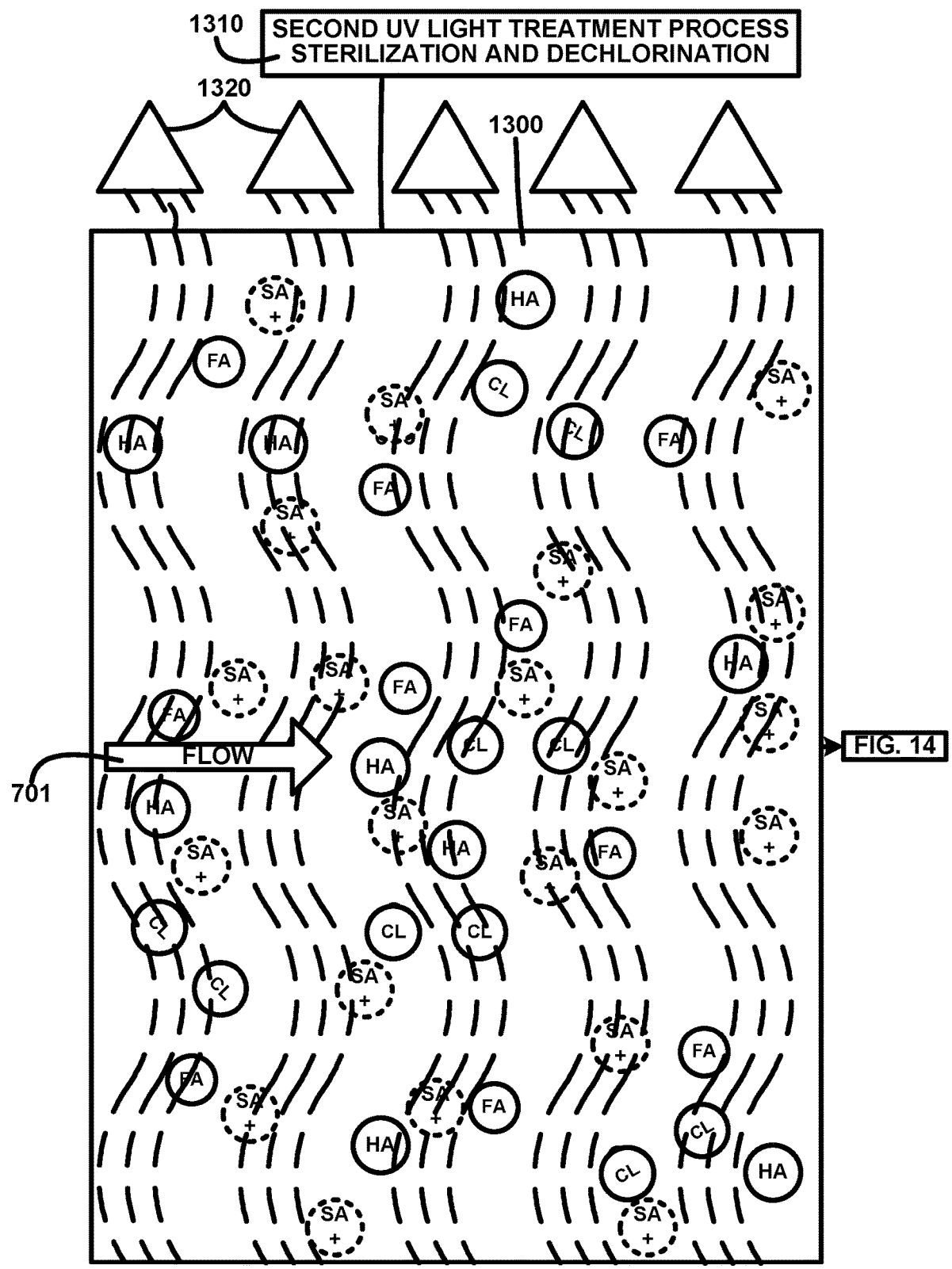
FIG. 13 shows for illustrative purposes only an example of second UV light treatment process sterilization and dechlorination of one embodiment.

Second UV Light Treatment Process Sterilization and Dechlorination:

FIG. 13 shows for illustrative purposes only an example of second UV light treatment process sterilization and dechlorination of one embodiment. FIG. 13 shows a continuation from FIG. 12 a second UV light treatment process sterilization and dechlorination 1310. A first post filtration chopped/pulverized humate-treated water mixture 1300 is passed through UV light beams created using second UV light treatment devices 1320 to expose the chopped/pulverized humate-treated water mixture 700 flow 701 to a higher intensity than the first UV light treatment process sterilization 1220 of FIG. 12 to kill any residual microorganism and to break apart chlorine $Cl_2$ molecules of one embodiment. The description of the process continues on FIG. 14.

Figure 14:
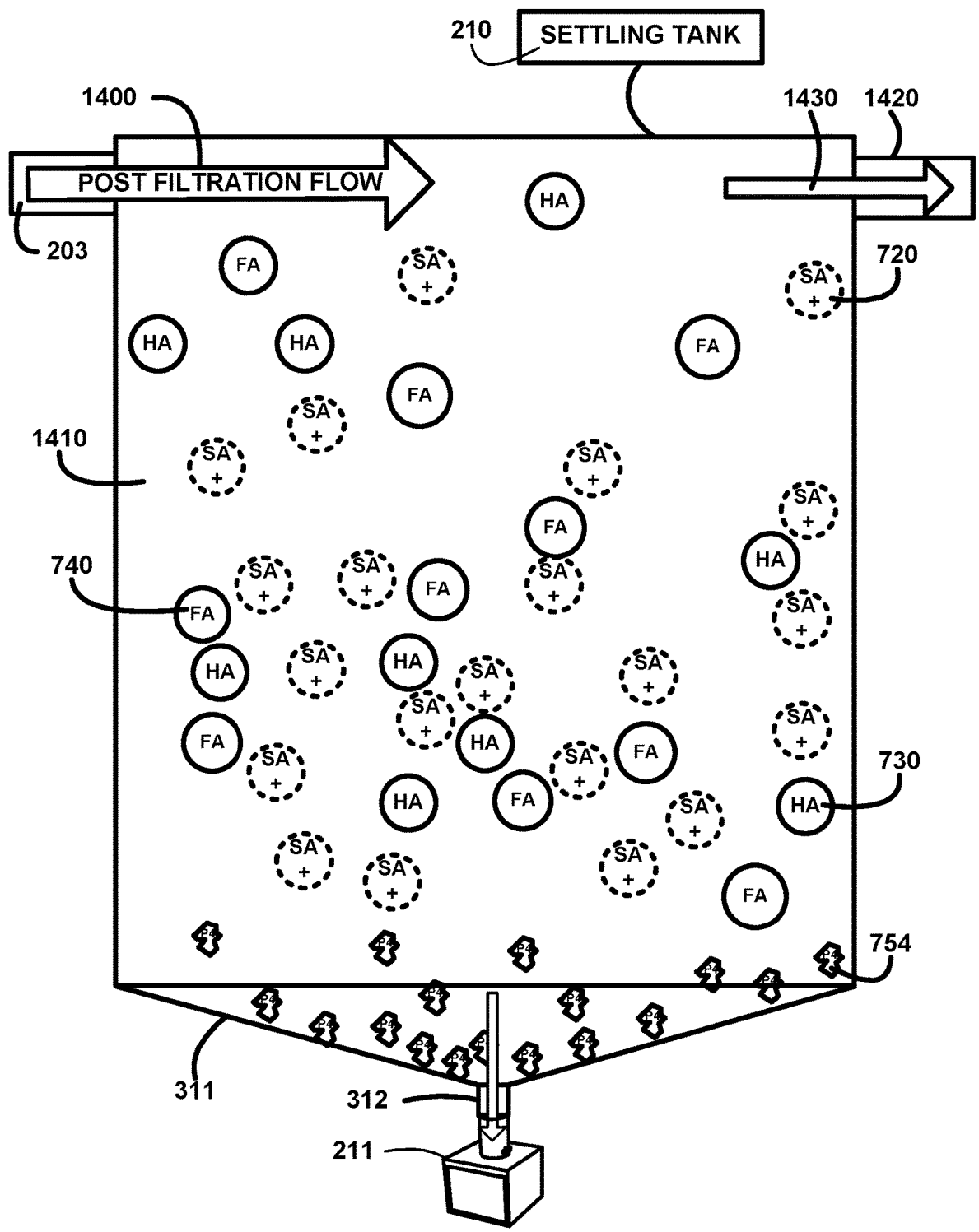
FIG. 14 shows for illustrative purposes only an example of a particulate filter settling tank of one embodiment.

Particulate Filter Settling Tank:

FIG. 14 shows for illustrative purposes only an example of a particulate filter settling tank of one embodiment. FIG. 14 shows a particulate filter settling tank 210 receiving the post filtration flow 1400 from the filtered humate-treated water mixture supply 203. The mixture 1410 includes pH treated water with suspended s+ soda ash molecules 720, HA humic acid molecules 730 and FA fulvic acid molecules 740. After filtration there may be residual suspended particulates p4 particulate size 4 754 or smaller in the mixture. The post filtration flow 1400 velocity slows when entering the settling tank 210. The reduced velocity allows residual suspended particulates to settle to the bottom of the settling tank 210 where the particulate waste accumulator funnel 311 accumulates the settled particulates and allows them to flow through the particulate waste disposal discharge pipe 312 and into the particulate disposal container 211. The remaining post filtration flow that is a settled humic-fulvic suspended mixture free of residual suspended particulates at the top of the settling tank 210 flows out 1430 of a settled humic-fulvic suspended mixture discharge pipe outlet 1420 of one embodiment.

Figure 15:
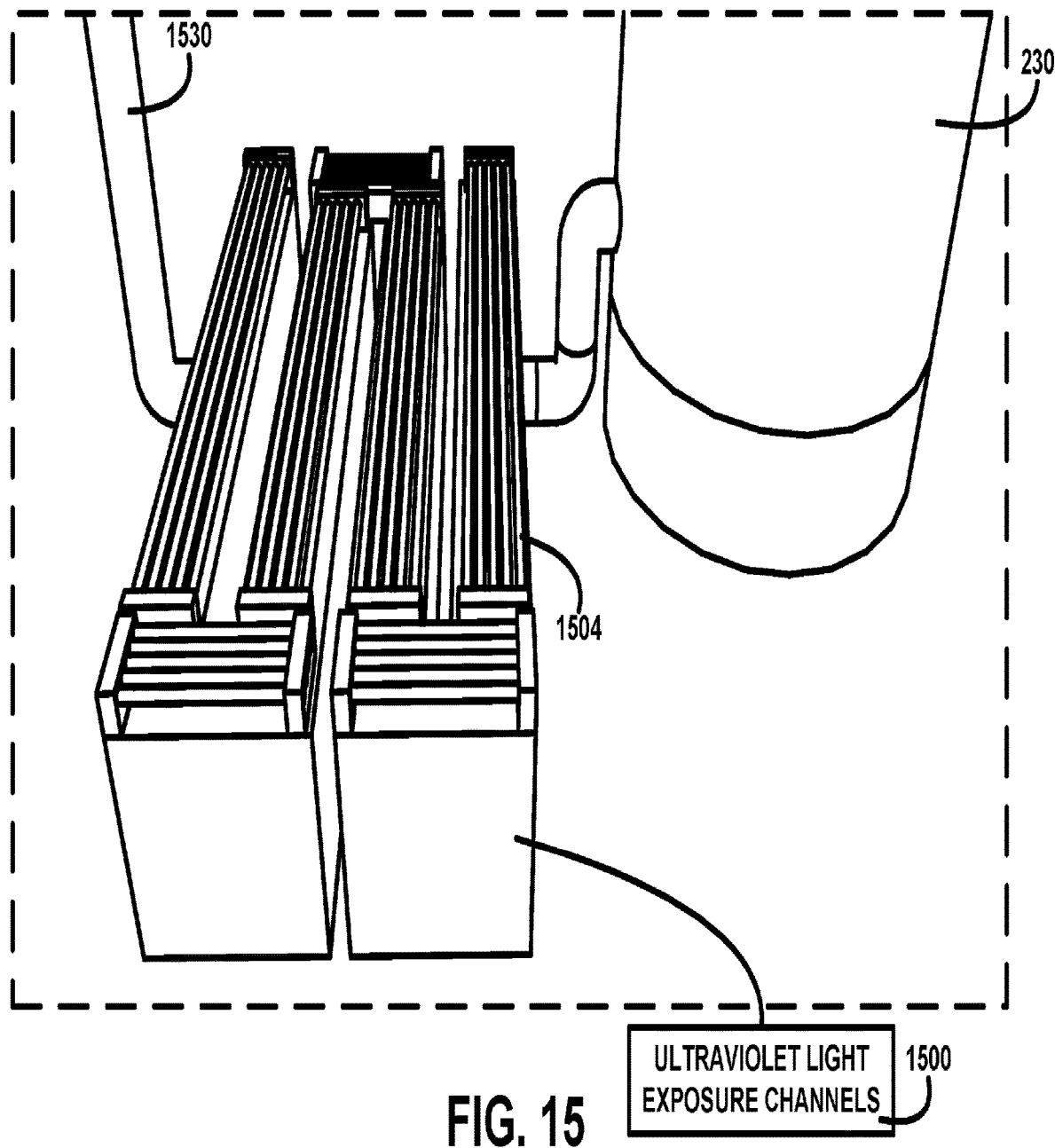
FIG. 15 shows for illustrative purposes only an example of ultraviolet light exposure channels of one embodiment.

Ultraviolet Light Exposure Channels:

FIG. 15 shows for illustrative purposes only an example of ultraviolet light exposure channels of one embodiment. FIG. 15 shows a settled humic-fulvic suspended mixture supply pipe 1530 supplying settled humic-fulvic suspended mixture to ultraviolet light exposure channels 1500. The ultraviolet light exposure bulbs 1504 are mounted to project UV light beams through the settled humic-fulvic suspended mixture flowing in the ultraviolet light exposure channels 1500. The ultraviolet light exposure bulbs 1504 and devices can include National Science Foundation (NSF) Certified UV Light Systems. The serpentine channel layout prolongs the time of the exposure to the fluid. The ultraviolet light exposure channels 1500 convey the exposed fluid into the first stage adsorption defluoridation device 230 of one embodiment.

Figure 16A:
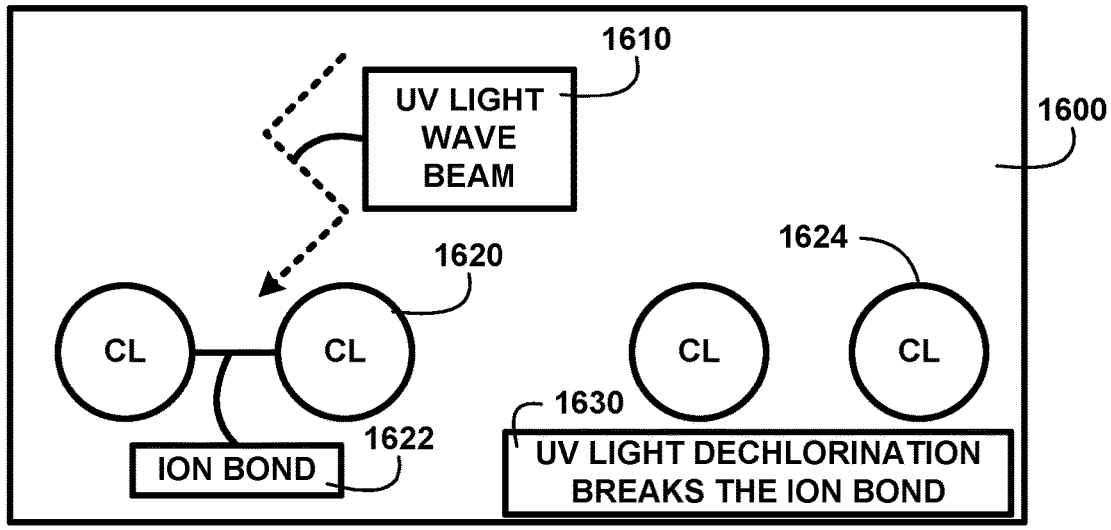
FIG. 16A shows for illustrative purposes only an example of UV light dechlorination of one embodiment.

UV Light Dechlorination:

FIG. 16A shows for illustrative purposes only an example of UV light dechlorination of one embodiment. FIG. 16A shows a UV light dechlorination 1600 process that projects at least one UV light wave beam 1610 into the mixture where chlorine has been detected. A chlorine $Cl_2$ molecule 1620 is held together by the force of an ion bond 1622. UV light dechlorination breaks the ion bond 1630 causing the two to separate into two free chlorine CI molecules 1624 that will dissipate more readily of one embodiment.

Figure 16B:
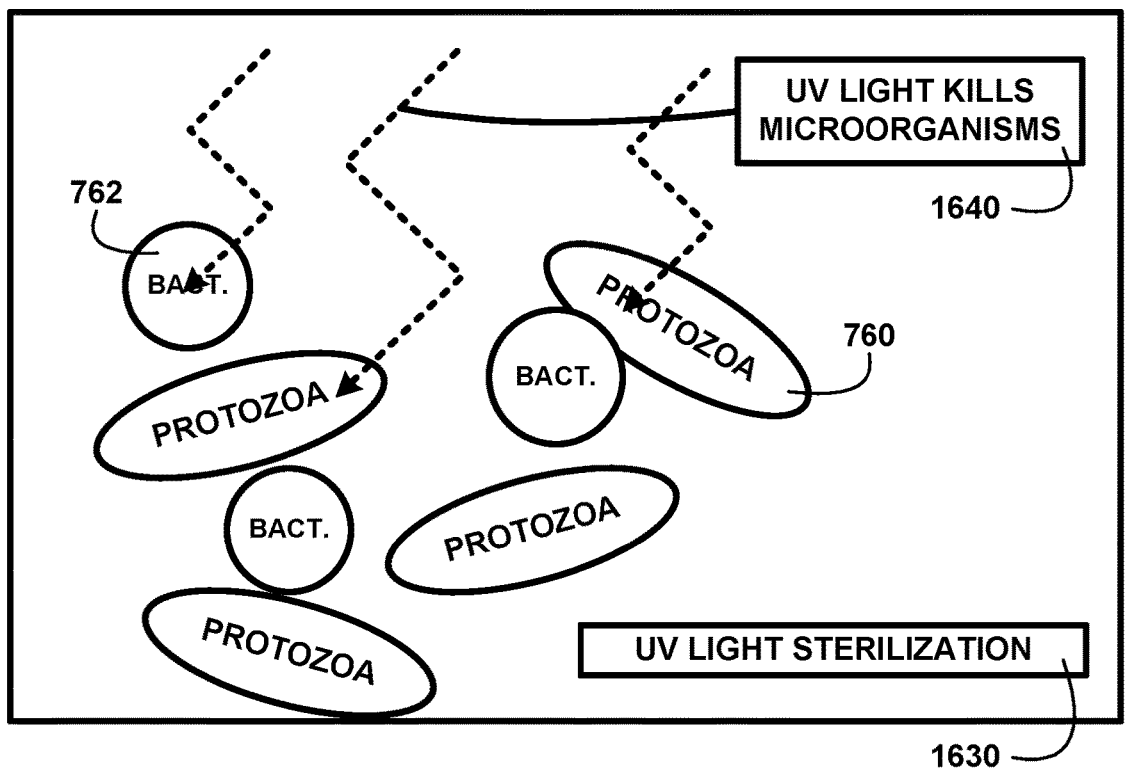
FIG. 16B shows for illustrative purposes only an example of UV light sterilization of one embodiment.

UV Light Sterilization:

FIG. 16B shows for illustrative purposes only an example of UV light sterilization of one embodiment. FIG. 16B shows a UV light sterilization 1630 process wherein UV light kills microorganisms 1640. For example the UV light wave beam intensity can kill the protozoa microorganism 760 and the bact. bacteria microorganism 762 and virus microorganisms of one embodiment.

Figure 17B:
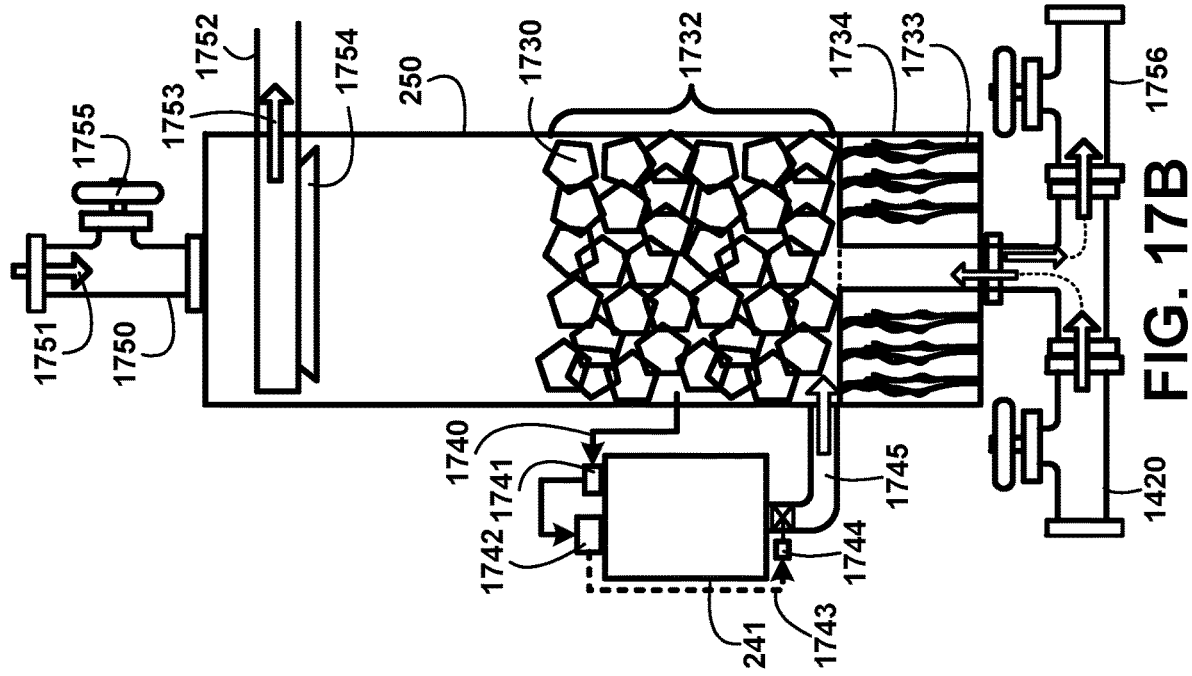
FIG. 17B shows for illustrative purposes only an example of a humic-fulvic acid separation chamber of one embodiment.
Figure 17A:
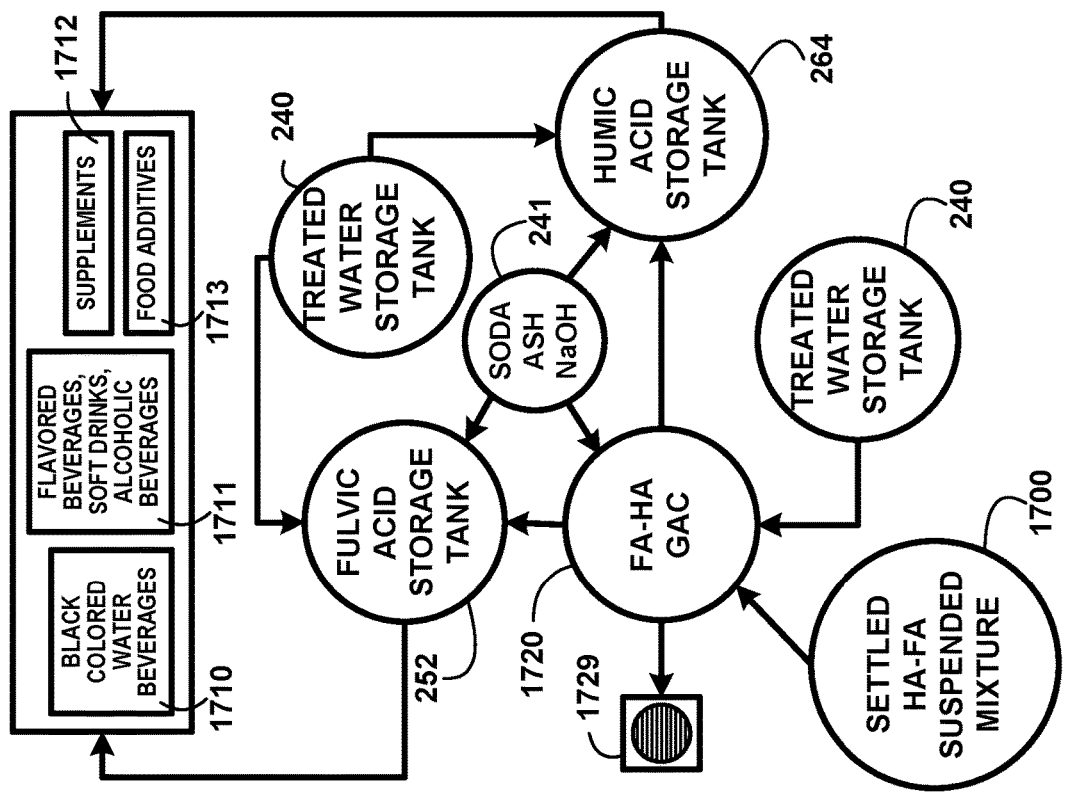
FIG. 17A shows for illustrative purposes only an example of a humic acid and fulvic acid separation and segregation process overview of one embodiment.

Settled Humic-Fulvic Suspended Mixture:

FIG. 17A shows for illustrative purposes only an example of a humic acid and fulvic acid separation and segregation process overview of one embodiment. FIG. 17 shows a settled HA-FA suspended mixture storage tank 1700 supplying the settled humic-fulvic suspended mixture to a fulvic acid-humic acid granular activated carbon (GAC) FA-HA GAC separation chamber 1720. Humic acid molecules adsorb to the granular activated carbon surfaces. When the separation and segregation processes are completed the remaining mixture and fresh flushing treated water are disposed of through discharge pipe and drain 1729 for recycling of one embodiment.

The separation process concentrates the fulvic acid molecules and segregates them to the fulvic acid storage tank 252 with temperature and pH control device 241. After the segregation of the fulvic acid molecules the humic acid molecules are separated from the granular activated carbon and are concentrated at the top of the separation chamber where they are segregated to the humic acid storage tank 264 with temperature and pH control device 241. A fresh treated water storage tank 240 with temperature control device and pH control device 241 supplies additional treated water when desired. The supplies of the fulvic acid molecules and humic acid molecules are used in the preparation products for human consumption including black colored water beverages 1710, flavored beverages, soft drinks, alcoholic beverages 1711, and supplements 1712 and food additives 1713 of one embodiment.

Humic-Fulvic Acid Separation Chamber:

FIG. 17B shows for illustrative purposes only an example of a humic-fulvic acid separation chamber of one embodiment. FIG. 17B shows a humic-fulvic acid separation chamber 250 with the settled humic-fulvic suspended mixture flowing into the separation chamber through the settled humic-fulvic suspended mixture discharge pipe outlet 1420. The settled humic-fulvic suspended mixture fills the separation chamber above the fulvic acid segregation vacuum device 1754 and covers the vacuum draw pipe 1752. A bed 1732 of activated carbon 1730 provides surface area to attract the humic acid molecules. The fulvic acid molecules rise to the top section of the separation chamber where they are drawn out of the separation chamber using the separation vacuum device 1754 to the fulvic acid storage tank 252 of FIG. 2 with temperature and pH control devices. When the concentration fulvic acid molecules is depleted from the settled humic-fulvic suspended mixture as indicated using a fulvic acid sensor the pH control device 241 is used to draw a sample of the mixture 1740 into a sensor 1741 to detect the pH level of the mixture.

A digital processor 1742 is used to calculate the volume of base to inject into the mixture 1745 to adjust the pH level and transmit a signal 1743 using a solenoid 1744 to open a valve to aid in the release of the humic acid molecules from the activated carbon surfaces. Burners 1733 included in a temperature control device 1734 are automatically ignited to raise the temperature of the remaining mixture to further aid in the release of the humic acid molecules from the activated carbon surfaces. The humic acid molecules rise to the top of the separation chamber and are draw out to the humic acid storage tank 264 of FIG. 2 with temperature and pH control devices. After segregation of the humic acid molecules a valve 1755 is opened to flush the separation chamber with fresh treated water 1751 through an inlet pipe 1750 to regenerate the activated carbon material 1730. The flushing regeneration water mixture is drained out the disposal discharge pipe 1756 for recycling of one embodiment.

Figure 17C:
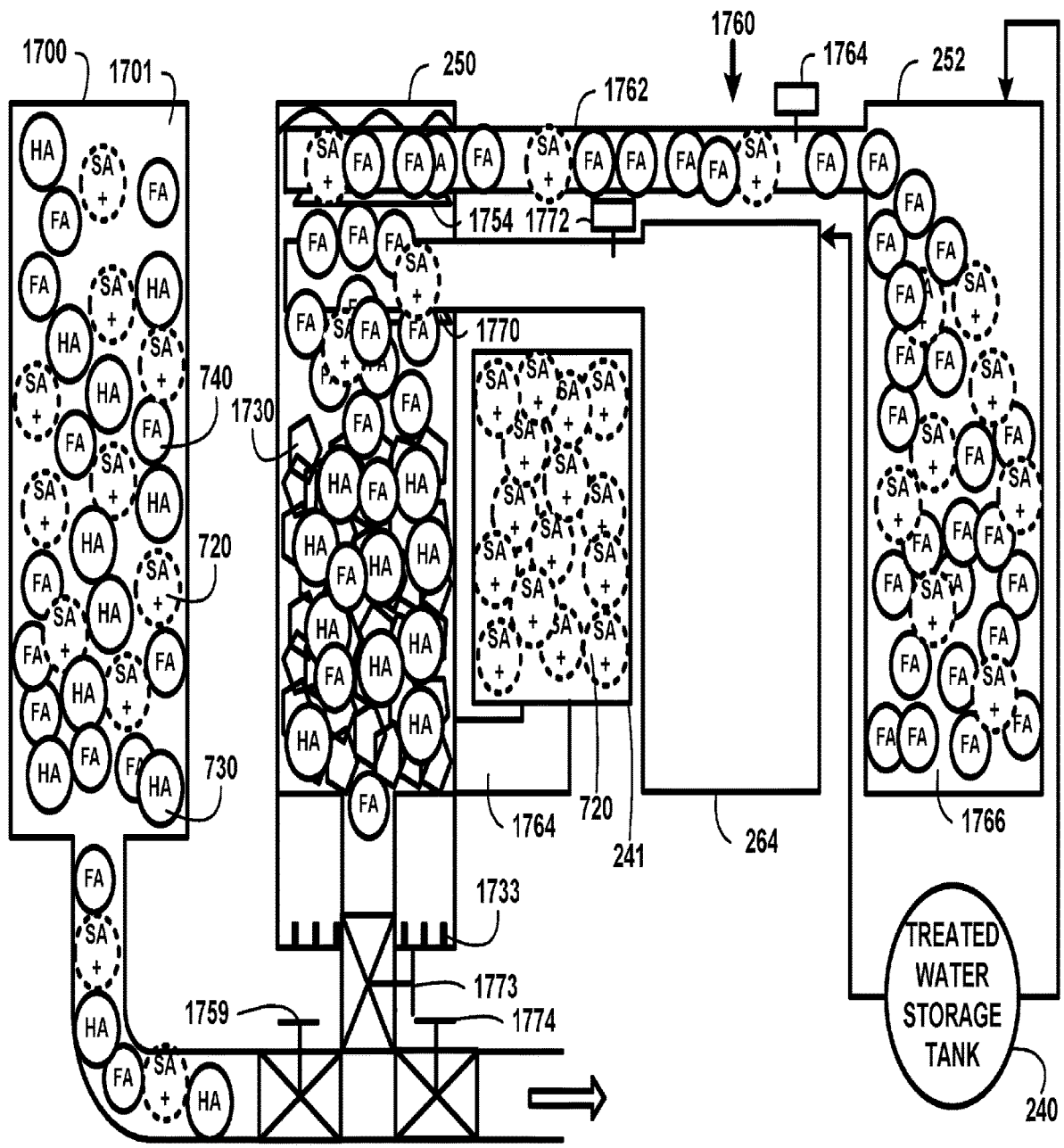
FIG. 17C shows for illustrative purposes only an example of fulvic acid separation and segregation of one embodiment.

Fulvic Acid Separation and Segregation:

FIG. 17C shows for illustrative purposes only an example of fulvic acid separation and segregation of one embodiment. FIG. 17C shows the presence of SA+ soda ash molecule 720, humic acid molecule 730, fulvic acid molecule 740 in a settled humic-fulvic suspended mixture supply 1701 in a settled HA-FA suspended mixture storage tank 1700. Piping conveying the mixture 1759 through an opened settled humic-fulvic suspended mixture supply valve 1759 and through an opened humic-fulvic acid separation chamber inlet valve 1773 for an activated carbon HA separation process 1760 of one embodiment.

The humic-fulvic acid separation chamber 250 contains a quantity of activated carbon 1730. When the humic-fulvic acid separation chamber 250 is filled to the top the settled humic-fulvic suspended mixture supply valve 1759 and humic-fulvic acid separation chamber inlet valve 1773 are closed. Humic acid molecules attach to the surfaces of the activated carbon. Fulvic acid molecules rise to the top of the separation chamber. A vacuum segregation of fulvic acid molecules 1762 is performed using a fulvic acid segregation vacuum device 1754. The fulvic acid segregation vacuum device 1754 draws the concentration fulvic molecules into the fulvic acid storage tank 252. Fulvic acid molecules suspended in treated water storage tank 1766 show in the fulvic acid storage tank 252. A fulvic acid detection device 1764 detects and measures the concentration of fulvic acid molecules. When the fulvic acid detection device 1764 measurements indicate the concentration fulvic acid molecules is depleted the fulvic acid segregation process stops of one embodiment.

Also showing is a humic acid molecules vacuum device 1770, humic acid detection device 1772, humic acid storage tank 264, pH control device 241, pH control device injection piping 1764, burners 1733, fresh treated water storage tank 240 and a humic-fulvic acid separation chamber discharge valve 1774 closed of one embodiment.

Figure 17D:
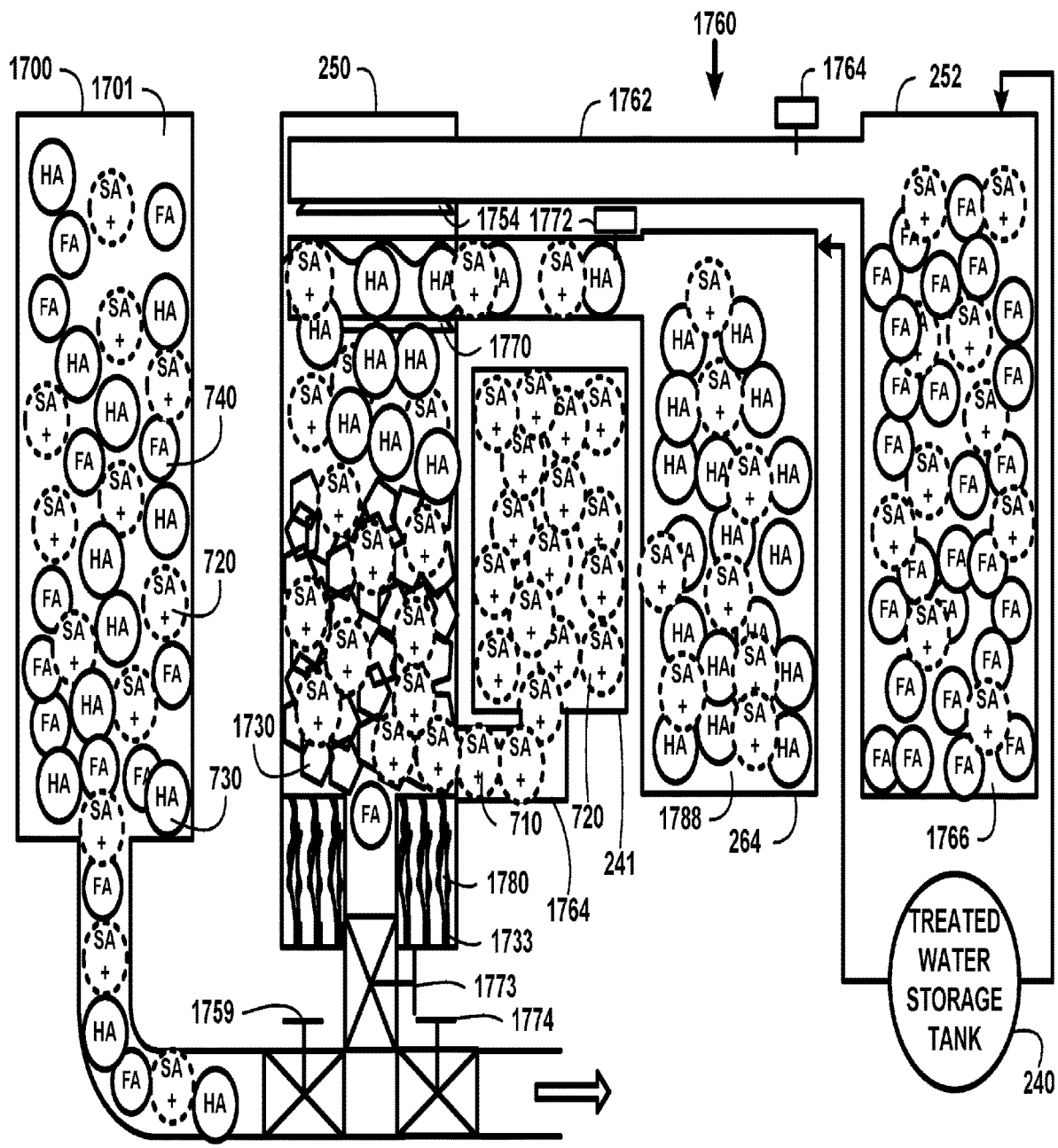
FIG. 17D shows for illustrative purposes only an example of humic acid separation and segregation of one embodiment.

Humic Acid Separation and Segregation:

FIG. 17D shows for illustrative purposes only an example of humic acid separation and segregation of one embodiment. FIG. 17D shows the presence of SA+ soda ash molecule 720, humic acid molecule 730, and fulvic acid molecule 740 in a settled humic-fulvic suspended mixture supply 1701 in a settled HA-FA suspended mixture storage tank 1700. Piping conveying the mixture 1759 through an opened settled humic-fulvic suspended mixture supply valve 1759 and through an opened humic-fulvic acid separation chamber inlet valve 1773 for an activated carbon HA separation process 1760. The humic-fulvic acid separation chamber 250 shows the activated carbon 1730 with attached humic acid molecules. The pH control device 241 with pH control device injection piping 1764 begins a process for injecting soda ash to raise pH 710. The burners 1733 are activated for ignited burners to raise the temperature 1780 of the mixture. Humic acid molecules are desorbed from the activated carbon and humic acid molecules rise to the top of the separation chamber.

A humic acid molecules vacuum device 1770 draws the concentrated humic acid molecules into the humic acid storage tank 264. Humic acid molecules suspended in treated water storage tank 1788 are showing in the humic acid storage tank 264. The humic acid detection device 1772 detects and measures the concentration of humic acid molecules in the humic acid molecules vacuum device 1770 flow. When the humic acid detection device 1772 measurements indicate the concentration humic acid molecules is depleted the humic acid segregation process stops. Also showing are the vacuum segregation of fulvic acid molecules 1762, fulvic acid molecules suspended in treated water storage tank 1766, fulvic acid detection device 1764, fulvic acid storage tank with temperature and pH control devices 252, and fulvic acid segregation vacuum device 1754 of one embodiment.

Figure 18A:
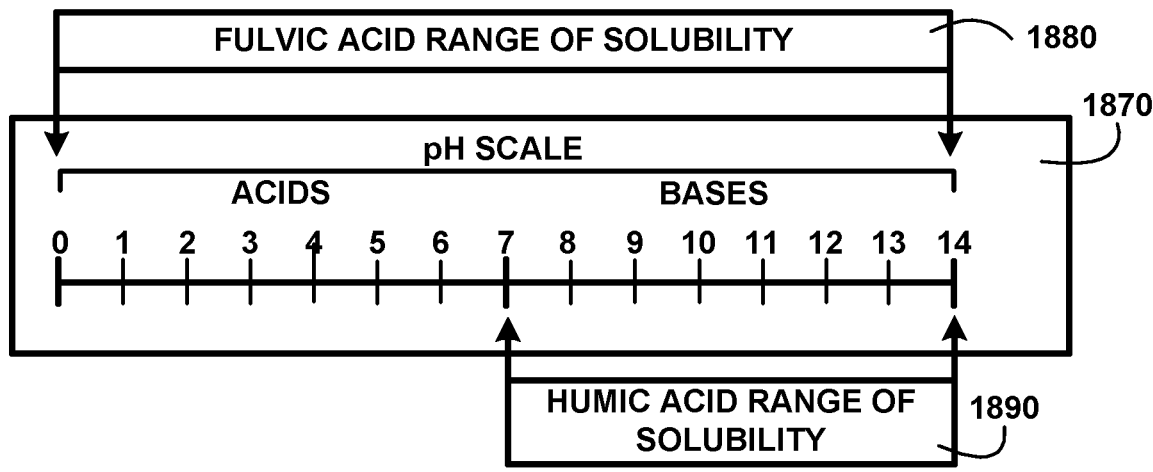
FIG. 18A shows for illustrative purposes only an example of a pH scale of one embodiment.

The process continues with a flushing process wherein fresh treated water is pumped into the humic-fulvic acid separation chamber 250 from the fresh treated water storage tank 240. The humic-fulvic acid separation chamber inlet valve 1773 and humic-fulvic acid separation chamber discharge valve 1774 are opened for discharging the remaining mixture and flush treated water for recycling of one embodiment.

pH Scale:

FIG. 18A shows for illustrative purposes only an example of a pH scale of one embodiment. FIG. 18A shows a pH scale 1870. The pH scale shows the ranges of pH are from 0 to 14. A humic acid range of solubility pH 7 to 14 1890 is limited to a base PH level. A fulvic acid range of solubility 1880 pH 0 to 14 means it is soluble at any pH level.

Figure 18B:
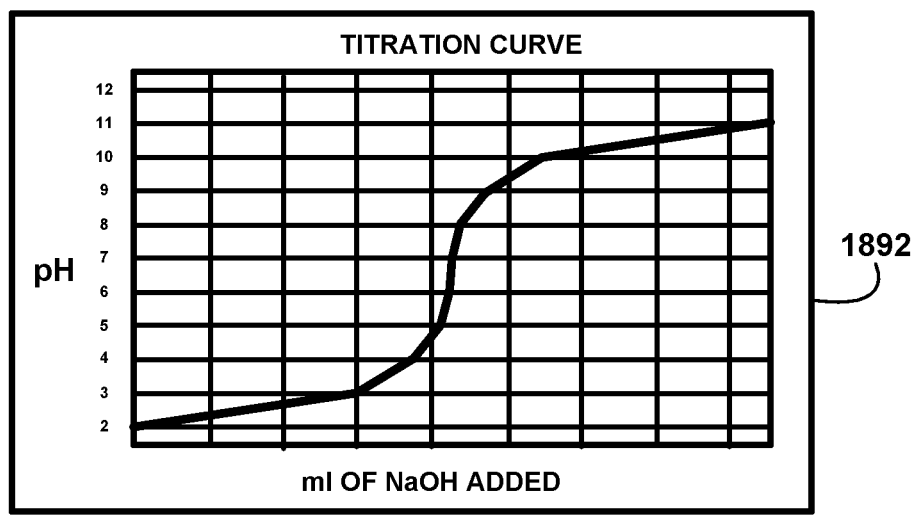
FIG. 18B shows a block diagram of an overview flow chart of titration curve of one embodiment.

Titration Curve:

FIG. 18B shows a block diagram of an overview flow chart of titration curve of one embodiment. FIG. 18B shows a titration curve 1892. Sodium hydroxide NaOH also called Soda Ash (SA) is a base material that when various amounts of ml of NaOH added to a solution raises the pH level from pH levels 2 to 12 based on the number of milliliters of NaOH added to the solution. The black water humic and fulvic acids extraction for human consumption and use method and devices uses at least one automated periodic sampling of the humate-treated water mixture at points along the process to check the pH level. If the pH is lower that a desired level NaOH is added to the solution in predetermined amounts to increase the base pH level to the desired level from the sampling detected level.

Figure 19A:
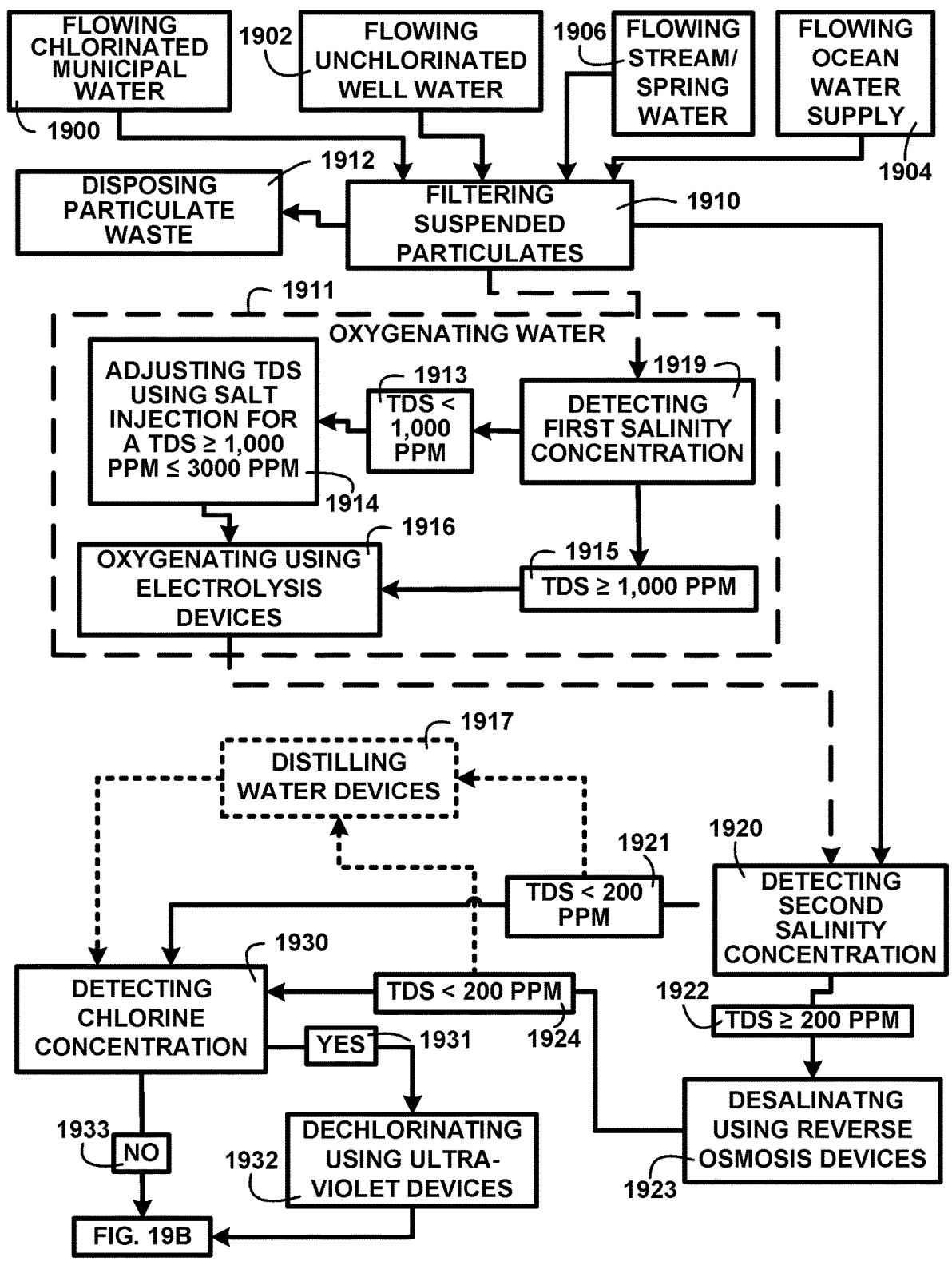
FIG. 19A shows a block diagram of an overview flow chart of treating water processes of one embodiment.

Treating Water Processes:

FIG. 19A shows a block diagram of an overview flow chart of treating water processes of one embodiment. FIG. 19A shows flowing chlorinated municipal water 1900, flowing unchlorinated well water 1902, flowing stream/spring water 1906, and flowing ocean water supply 1904 as water sources that may be used for the treating water processes. At least one of the water sources is processed for filtering suspended particulates 1910. The particulates removed are conveyed for disposing particulate waste 1912.

A next process can include a process for oxygenating water 1911 beginning with a process for detecting a first salinity concentration 1919. Oxygenating water 1911 can include an electrolysis process of water with a salinity level to promote conductivity of the electrolysis charges through the volume of water. A detecting first salinity concentration 1919 process determines the salinity of the water. Should the water have a total dissolved salt (TDS) concentration where TDS<1,000 ppm 1913 the process continues for adjusting TDS using salt injection for a TDS≥1,000 ppm≤3000 ppm 1914 and the water is automatically diverted for oxygenating using electrolysis devices 1916. If the detecting first salinity concentration 1919 process determines the salinity of the water has TDS≥1,000 ppm 1915 the water is automatically diverted for oxygenating using electrolysis devices 1916. After an oxygenating water 1911 process is complete the salinity of the water is reduced to a suitable drinking water concentration level.

A next process can include a process for detecting a second salinity concentration 1920 of the water source. Total dissolved salt (TDS) is a measure of the salts suspended in liquid generally measured in parts per million (ppm). The black water humic and fulvic acids extraction for human consumption and use method and devices targets TDS<200 ppm 1921 for human consumption which is a level generally found in drinking water. Automated sampling of the water source is used for obtaining a sample that is fed into an automated chemical analyzer for detecting salinity concentration 1920. A TDS<200 ppm 1921 automatically initiates a diversion of the flow of the water source to the next process. A TDS≥200 ppm 1922 automatically initiates a diversion of the flow of the water source for desalinating using reverse osmosis devices 1923 to reduce the salinity to a TDS<200 ppm 1924. Once the analysis reaches a salinity of a TDS<200 ppm 1921 the flow is automatically diverted to a next process.

A next process can include creating distilled water using distilling water devices 1917. After a distilling water process is complete the process continues to a process for detecting chlorine concentration 1930.

A next process can include a process for detecting chlorine concentration 1930. A detected chlorine concentration with a yes 1931 or positive for the presence of chlorine ($Cl_2$) initiates an automatic diversion of the water source flow for dechlorinating using ultra-violet devices 1932. Upon complete of dechlorination the flow is automatically diverted to the next process. A detecting chlorine concentration 1930 with a result of no 1933 or negative detection the presence of chlorine automatically diverted to the additional processes described in FIG. 19B.

Figure 19B:
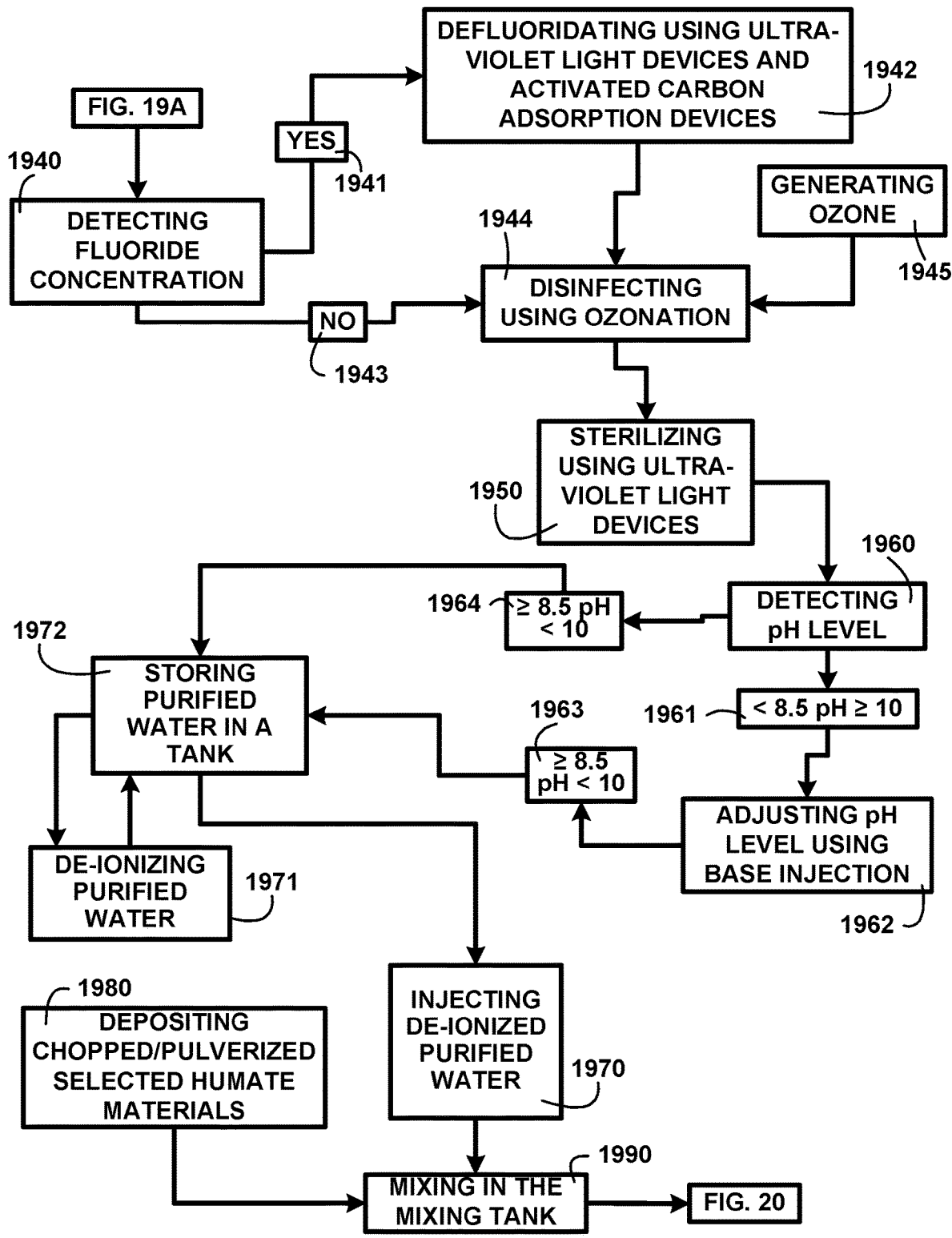
FIG. 19B shows a block diagram of an overview flow chart of treating water additional processes of one embodiment.

Treating Water Additional Processes:

FIG. 19B shows a block diagram of an overview flow chart of treating water additional processes of one embodiment. FIG. 19B shows treating water additional processes continuing from FIG. 19A including a process for detecting fluoride concentration 1940. A detecting fluoride concentration 1940 analysis result indication yes 1941 a positive detection of fluoride in the water source automatically diverts the flow of the water source to a process for defluoridating using ultra-violet light devices and activated carbon adsorption devices 1942. Once an automatic sampling analysis shows the defluoridation process is complete the water source flow is diverted to the next process. The next process uses generating ozone 1945 for disinfecting using ozonation 1944. An initial detecting fluoride concentration 1940 analysis result indication no 1943 a negative finding that no fluoride is present the water source is diverted to the next process disinfecting using ozonation 1944. Following ozonation is a process for sterilizing using ultra-violet light 1950.

A first step in the sterilizing using ultra-violet light devices 1950 process is automatically taking a sampling of the water source for detecting pH level 1960. An automatic detecting pH level 1960 result showing a <8.5 pH≥10 1961 automatically diverts the flow of the water source flow for adjusting pH level using base injection 1962. Once a ≥8.5 pH<10 1963 is detected after the adjusting pH level using base injection 1962 process the water source flow is automatically diverted for storing purified water in a tank 1972 for the next process. If the initial automatic detecting pH level 1960 shows a ≥8.5 pH<10 1964 the water source flow is automatically diverted for storing purified water in a tank 1972 for the next process for de-ionizing purified water 1971. The processing continues for adding de-ionized purified water 1970 for mixing in the mixing tank 1990. Once the treated water source is injected into the mixing tank 171 of FIG. 1 a process begins for depositing chopped/pulverized selected humate materials 1980 for mixing in the mixing tank 1990 with the injected treated water. The process descriptions continue in FIG. 20.

Figure 20:
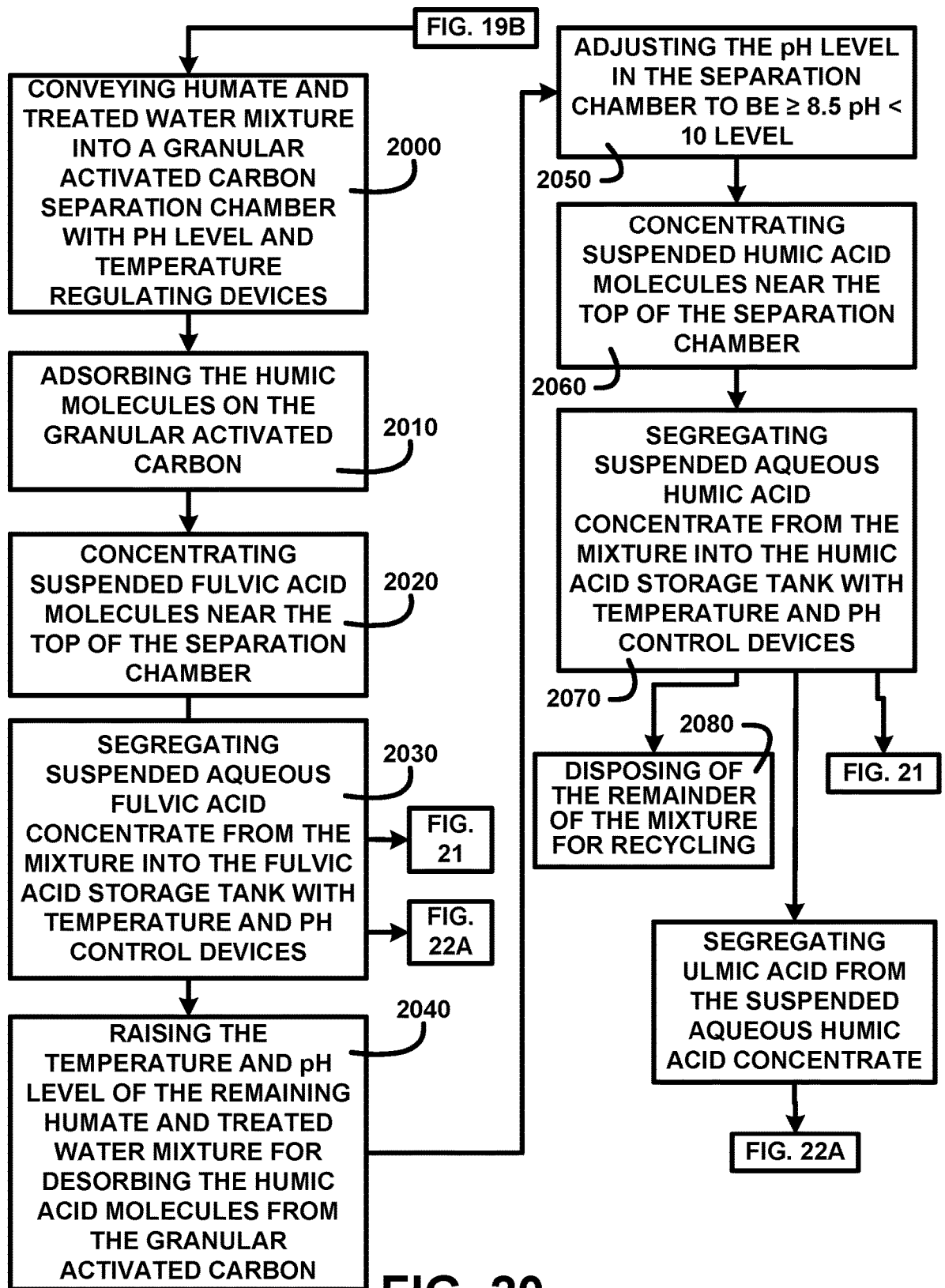
FIG. 20 shows a block diagram of an overview flow chart of extraction and segregation of humic and fulvic acids of one embodiment.

Extraction and Segregation of Humic and Fulvic Acids:

FIG. 20 shows a block diagram of an overview flow chart of extraction and segregation of humic and fulvic acids of one embodiment. FIG. 20 shows the continuation of the processing from FIG. 19 including conveying humate and treated water mixture into a granular activated carbon separation chamber with pH level and temperature regulating devices 2000. Adsorbing the humic molecules on the granular activated carbon 2010. Concentrating suspended fulvic acid molecules near the top of the separation chamber 2020 then segregating suspended aqueous fulvic acid concentrates from the mixture into the fulvic acid storage tank with temperature and pH control devices 2030. The aqueous fulvic acid concentrate having been removed the process continues by raising the temperature and PH level of the remaining humate and treated water mixture for desorbing the humic acid molecules from the granular activated carbon 2040. A sampling of the remaining humus and treated water mixture is automatically analyzed to determine the pH level. If the sampling is <8.5 pH≥10 the pH control device automatically initiates adjusting the pH level in the granular activated carbon separation chamber to be ≥8.5 pH<10 level 2050 and cause the release of the humic acid molecules from the activated carbon materials. Concentrating suspended humic acid molecules near the top of the separation chamber 2060. Segregating suspended aqueous humic acid concentrate from the mixture into the humic acid storage tank with temperature and pH control devices 2070. Disposing of the remainder of the mixture for recycling 2080. Description of the processing continues in FIG. 21.

Figure 21:
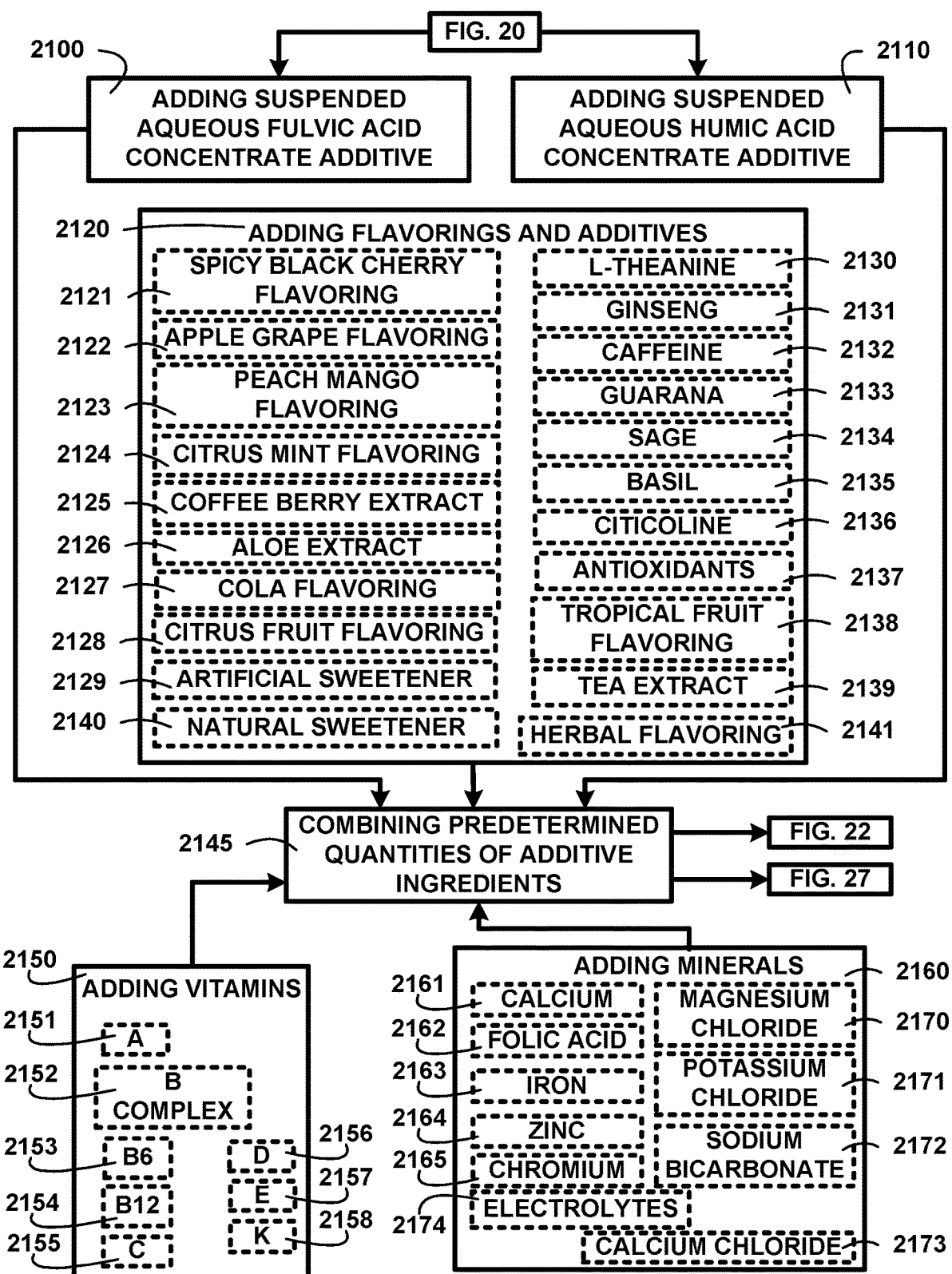
FIG. 21 shows a block diagram of an overview flow chart of creating products for human consumption and use with humic and fulvic acids of one embodiment.

Creating Products for Human Consumption and Use:

FIG. 21 shows a block diagram of an overview flow chart of creating products for human consumption and use with humic and fulvic acids of one embodiment. FIG. 21 shows processing continuing from FIG. 20 with adding suspended aqueous fulvic acid concentrate additive 2100 and adding suspended aqueous humic acid concentrate additive 2110. Products for human consumption can also be adding flavorings and additives 2120, spicy black cherry flavoring 2121, apple grape flavoring 2122, peach mango flavoring 2123, citrus mint flavoring 2124, coffee berry extract 2125, aloe extract 2126, cola flavoring 2127, citrus fruit flavoring 2128, artificial sweetener 2129, I-theanine 2130, *ginseng* 2131, caffeine 2132, guarana 2133, sage 2134, basil 2135, citicoline 2136, antioxidants 2137, tropical fruit flavoring 2138, tea extract 2139, natural sweetener 2140, herbal flavoring 2141, and other flavorings and additives.

The ingredients being added include adding vitamins 2150 including A 2151, B complex 2152, B6 2153, B12 2154, C 2155, D 2156, E 2157, K 2158, and other vitamins. The ingredients being added include adding minerals 2160, calcium 2161, folic acid 2162, iron 2163, zinc 2164, chromium 2165, magnesium chloride 2170, potassium chloride 2171, sodium bicarbonate 2172, calcium chloride 2173 and electrolytes 2174. Combining predetermined quantities of additive ingredients 2145 is then used in processing described in FIG. 22.

Figure 22:
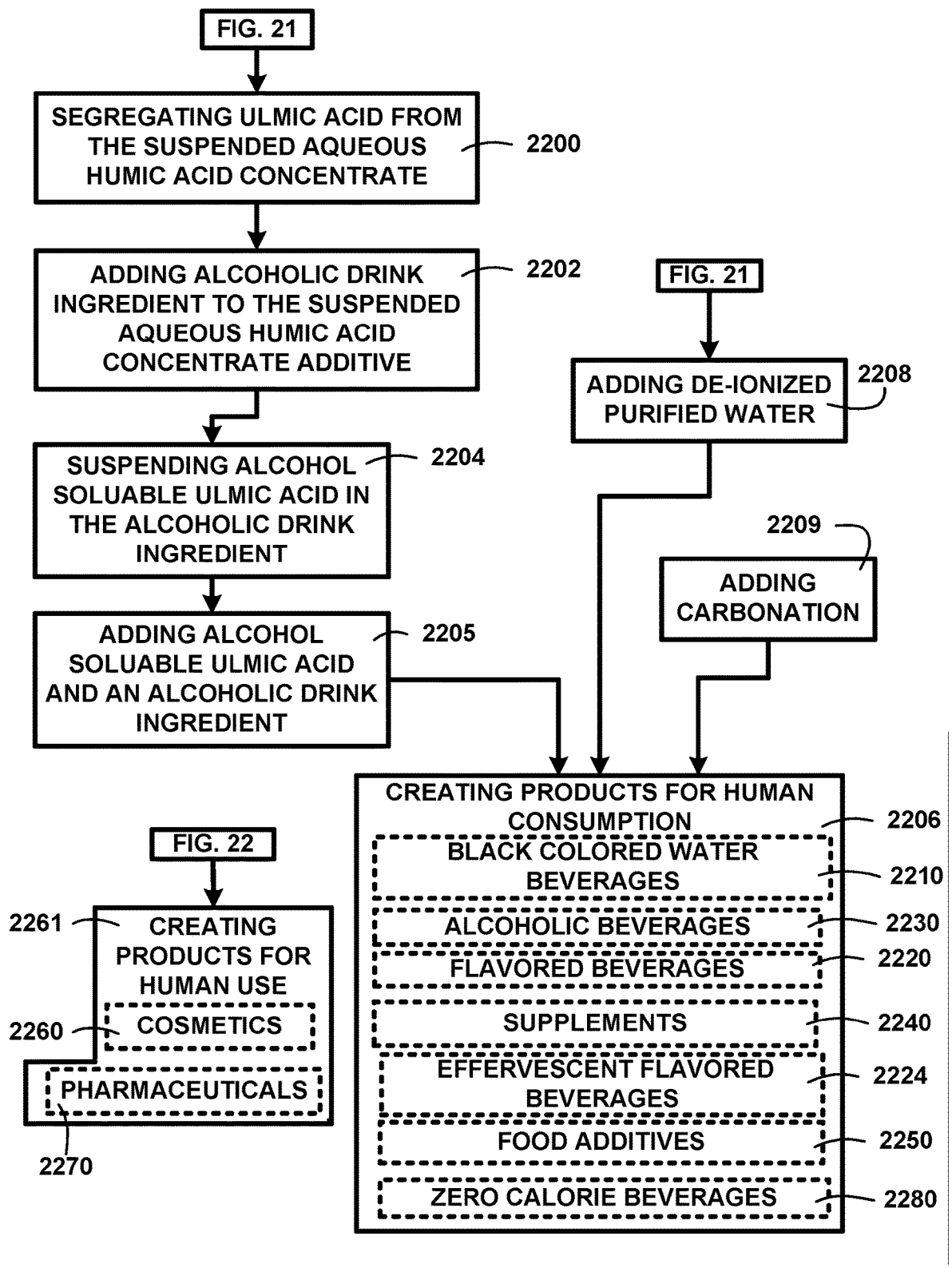
FIG. 22 shows a block diagram of an overview flow chart of a continuation of creating products for human consumption and use with humic and fulvic acids of one embodiment.

Products for Human Consumption and Use:

FIG. 22 shows a block diagram of an overview flow chart of a continuation of creating products for human consumption and use with humic and fulvic acids of one embodiment. FIG. 22 shows a continuation of a process from FIG. 21 for creating products for human consumption. The combining predetermined quantities of additive ingredients 2145 of FIG. 21 further includes adding de-ionized purified water 2208 and adding carbonation 2209. Combining ingredients for alcoholic beverages includes segregating ulmic acid from the suspended aqueous humic acid concentrate 2200, adding alcoholic drink ingredient to the suspended aqueous humic acid concentrate additive 2202, suspending alcohol soluble ulmic acid in the alcoholic drink ingredient 2204, and adding alcohol soluble ulmic acid and an alcoholic drink ingredient 2205.

Black water alcoholic beverages will include a flavoring based on the type of alcohol added to the mix including beers and liquor or hard liquor. Humic acids contain an alcohol-soluble portion of the humic fraction named ulmic acid. The ulmic acid will be conveyed to the bottling processes through a separate ulmic acid discharge piping system. Humic and fulvic mineral extraction method and beverage for human consumption alcoholic beverages will be mixed with the ulmic acid and fulvic acids in predetermined volumes of one embodiment.

The processes of combining predetermined quantities of additive ingredients 2145 of FIG. 21 are followed by processes for creating products for human consumption 2206 including black colored water beverages 2210, flavored beverages 2220, effervescent flavored beverages 2224, alcoholic beverages 2230, supplements 2240, food additives 2250, and zero calorie beverages 2280. FIG. 22 shows a continuation of a process from FIG. 21 for creating products for human use 2261 including cosmetics 2260, and pharmaceuticals 2270.

Combinations of the ingredients can produce different tastes and consumer benefits including improving a consumer's mood, vitamins and nutrients providing a consumer energy boost, improving a person focus, providing newly focused mental faculties, providing trace minerals that supply electrolytes, antioxidants and amino acids a consumer's body needs, helps boost a consumer's immune system and other benefits. Combining quantities of additive ingredients 2145 of FIG. 21 and selecting some but not all of the ingredients are varied to target specific benefits and taste in the products for human consumption. The black water humic and fulvic acids extraction for human consumption and use method and devices not only removes harmful chemicals in the processing but also does not use other chemicals that can pose a health risk to consumers of products that include humic and fulvic acids extracted using potentially harmful chemicals in the extraction processing. At least annually sample(s) consisting of primary containers of product of unit packages of product shall be tested by an approved competent commercial laboratory and the results of the at least annual test results will be keep on file and logged into a black water bottling process server of one embodiment.

Figure 23A:
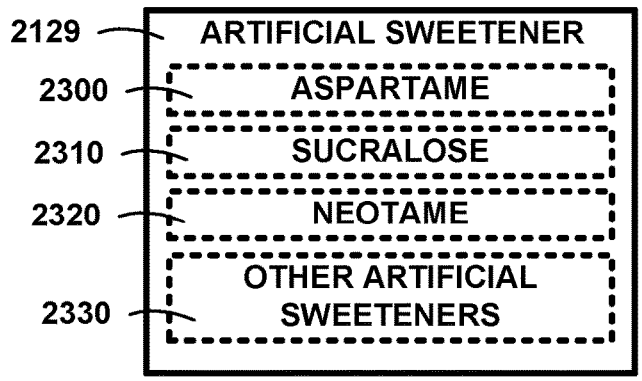
FIG. 23A shows a block diagram of an overview of artificial sweetener ingredients of one embodiment.

Artificial Sweetener Ingredients:

FIG. 23A shows a block diagram of an overview of artificial sweetener ingredients of one embodiment. FIG. 23A shows a partial list of the artificial sweetener 2129 additive ingredient used for creating products for human consumption 2206 of FIG. 22. The artificial sweetener 2129 additive ingredients include aspartame 2300, sucralose 2310, neotame 2320, and other artificial sweeteners 2330 of one embodiment.

Figure 23B:
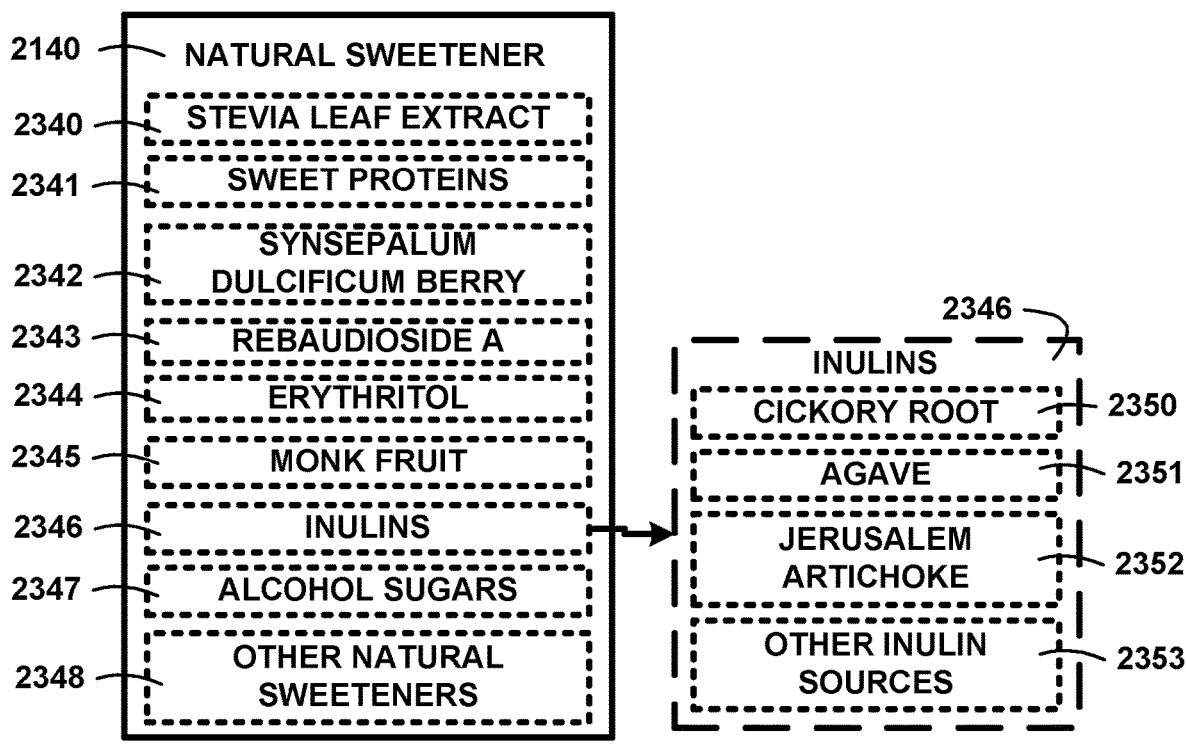
FIG. 23B shows a block diagram of an overview of natural sweetener ingredients of one embodiment.

Natural Sweetener Ingredients:

FIG. 23B shows a block diagram of an overview of natural sweetener ingredients of one embodiment. FIG. 23B shows a partial list of the natural sweetener 2140 additive ingredient used for creating products for human consumption 2206 of FIG. 22. The natural sweetener 2140 additive ingredients include stevia leaf extract 2340, sweet proteins 2341, *Synsepalum dulcificum* berry 2342, rebaudioside a 2343, erythritol 2344, monk fruit 2345, inulins 2346, alcohol sugars 2347, and other natural sweeteners 2348. Some of the natural sweetener 2140 additive ingredients have no or low levels of calories. The inulins 2346 group of natural sweetener 2140 additive ingredients includes chicory root 2350, agave 2351, Jerusalem artichoke 2352 and other inulin sources 2353.

Inulin is not digested or absorbed in the stomach. It goes to the bowels where bacteria are able to use it to grow. It supports the growth of a special kind of bacteria that are associated with improving bowel function and general health. Inulin decreases the body's ability to make certain kinds of fats. Inulin received no-objection status as generally recognized as safe (GRAS) from the US Food and Drug Administration (FDA). Inulin is not digested by enzymes in the human alimentary system, contributing to its functional properties: reduced calorie value, dietary fiber and prebiotic effects of one embodiment.

Figure 24:
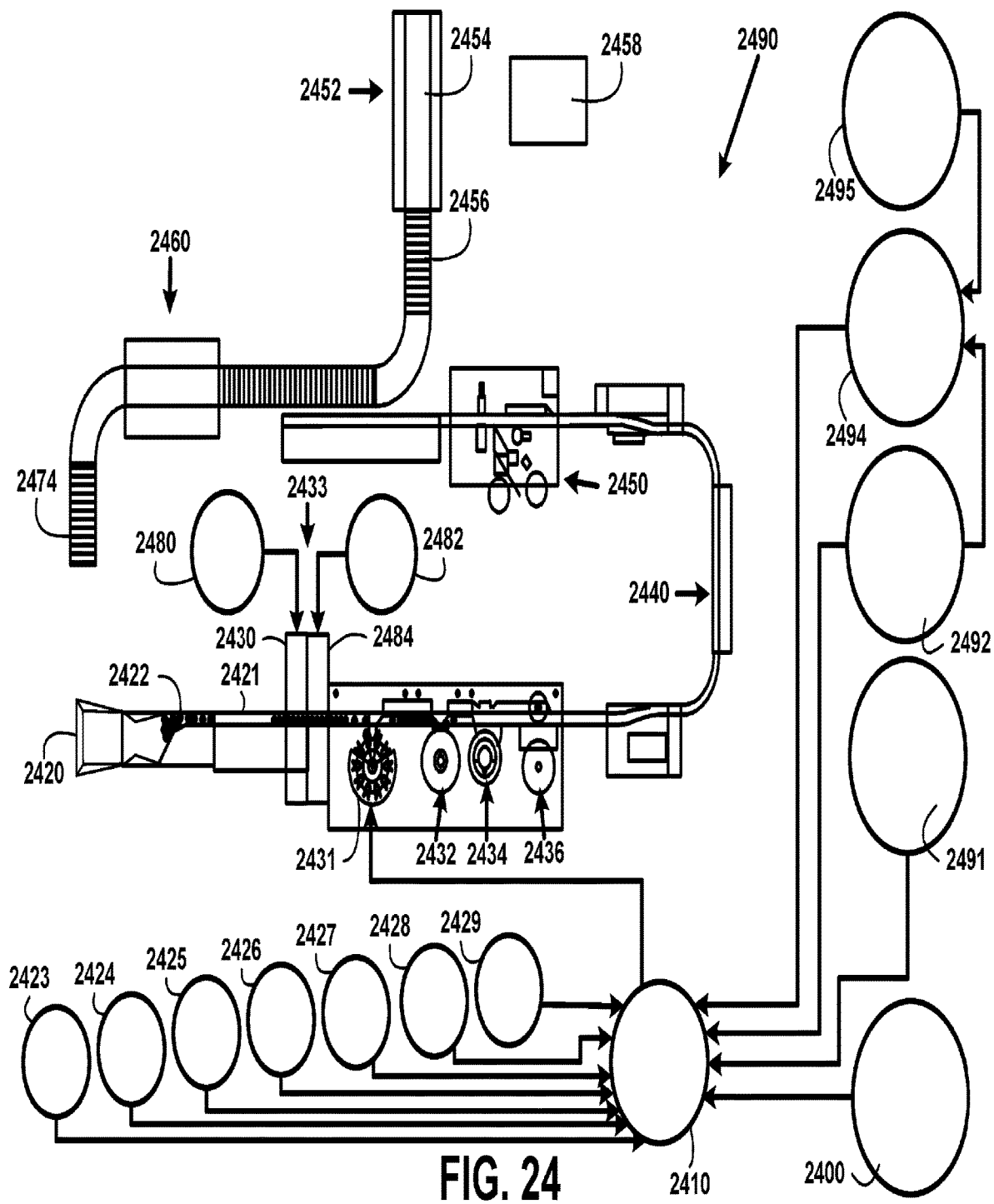
FIG. 24 shows for illustrative purposes only an example of a black water bottling process of one embodiment.

Black Water Bottling Process:

FIG. 24 shows for illustrative purposes only an example of a black water bottling process of one embodiment. In the following description the terms "bottle" and "bottling" have the meaning of a "beverage container" including a glass bottle, a can including an aluminum can, a food grade plastic bottle, a food grade beverage container that is biodegradable, a beverage container made with an ultraviolet protective tinting or exterior coating, and wherein each type of beverage container may of any volume capacity. The beverage container can include an opening device including a "pop top" opening device, a screw-on cap made of a food grade plastic or aluminum, a crimped cap, a cork, a sealed detection device and other types of capping devices.

FIG. 24 shows a black water bottling process beginning with an empty bottle supply bin 2420 where empty bottles are positioned for processing through an empty bottle conveyor alignment 2422 apparatus. The empty bottles are fed in a single row onto a single empty bottle conveyor 2421. The process includes a de-ionized purified water empty bottle sanitation station 2430 where the bottles are rinsed clean in a bottle cleaning area 2433. The sanitizing rinse includes de-ionized purified water from an empty bottle sanitation station de-ionized purified water supply tank 2480 and can include heating the de-ionized purified water to a temperature ranging from 110° F. to 180° F. The elevated temperature and de-ionization of the purified water sanitizes the bottle and removes minerals that could remain on the surfaces of the bottles. The minerals that are removed may be some of the same minerals being added later in the processing, but the amount of the minerals in the purified water rinsing cycle may be unknown and may cause a quantity of mineral in the final beverage formulation greater than a predetermined amount to be added. The rinse water used is recycled to the treating water processes described in FIG. 19A and FIG. 19B.

All bottling facilities shall apply for and retain on file in the bottling facilities current certificates or notifications of approval issued by the government agency or agencies approving the plant's source and supply of product water and operations water. All required certificates or notifications of approval shall be available for review at reasonable times. Bottling facilities can include for example an empty bottle filling station 2431 room with tight walls, ceilings, and self-closing doors not shown separate from other bottling operations with double self-closing passage doors that cannot open directly into any room for protection against contamination. Conveyor openings are sized to permit passage of containers. Processing operations can include a sealed system under internal air pressure to prevent infiltration of outside air that may contain particulates and microbial organisms and adequate protection to preclude contamination of the water and the processing system. Adequate ventilation is included to minimize condensation in processing rooms, bottling rooms, and in a bottle cleaning area 2433 for washing and sanitizing bottles.

The bottle cleaning area 2433 can include an enclosed room, not shown, for preventing post-sanitizing contamination of the bottles. The empty bottle filling station 2431 can include a sealed room not shown that include double passage doors to prevent contamination from outside air. All double passage door passage ways will include positive air pressure to prevent infiltration of outside air and floor vacuum exhaust apparatus to remove soil, dust and other clothing contaminates possibly on personnel clothing. The floors will include footwear brushing apparatus to permit personnel to brush off any debris on the soles of their footwear. The turbulent positive air pressure blowers will include ultrafiltration and sufficient turbulence to knock lose any particulates on their clothing. Positive air pressure shall be free of oil, dust, rust, excessive moisture, and extraneous materials and shall not affect the bacteriological quality of the water and should not adversely affect the flavor, color, or odor of the water.

All product water and operations water supplies are properly located, protected, and operated, easily accessible, adequate, and of a safe, sanitary quality compliant at all times with the applicable laws and regulations of the government agency or agencies having jurisdiction. Finished bottled water must comply with bottled water quality standards.

Bottling facilities can include locker and lunchrooms that are separate from plant operations and storage areas and include self-closing doors. Procedures will be established to maintain locker and lunchrooms in a clean and sanitary condition with refuse containers should be provided. Bottling materials and supplies will not be stored in locker or lunchrooms.

Next the empty bottles are processed through an empty bottle air cleaner station 2484. The filter compressed air is injected into the empty bottles from an empty bottle air cleaner station compressed air supply tank 2482. This dries the empty bottles and prevents any particulates from the air from remaining in the empty bottles. Bottles are then conveyed into an empty bottle filling station 2431. The black water bottling process includes but is not shown in FIG. 24 at least one test valve at each supply piping coupled to a supply tank for taking samples of for example waters, liquids and powders. The samples taken are used for testing of microbial and non-organic substances at least weekly. Microbial testing includes for example heterotrophic plate count, coliforms, mold, yeast, *Pseudomonas aeruginosa*, bacteria, protozoa, fungi, viruses, *E. coli*, and other microorganisms and bacteria.

The samples are taken at a predetermined periodic basis. If any coliform organisms are detected, follow-up testing must be conducted to determine whether any of the coliform organisms are *E. coli*. Sample test results reports are logged into the black water bottling process server including date of sampling, type of product sampled, unit package production code, and results of the analysis and reported to appropriate agencies. While samples are tested in approved laboratories there are also on-site automated testing devices to preform immediate preliminary test results. The on-site automated testing devices are activated by a black water bottling process server signal to each testing device to open the at least one testing valve using a solenoid and process the sample through the on-site automated testing device for detecting microbial and non-organic substances.

If the preliminary test results indicate the presence of a targeted microbial organism, the on-site automated testing devices transmit an alert signal to activate a pulsing red light at the location of the at least one test valve, activates an audio alarm and activate a shut-down of the additive supply valve to prevent contamination beyond that point. The automated testing devices transmitted alert signal and test results also is received by a black water bottling process server which relays the signal over a WI-FI communication device to supervisory and management personnel using texting, email and a recorded alert message over a voice communication.

Other on-site automated testing devices automatically test a sample for targeted non-organic substances including for example minerals, humic and fulvic acid quantities, a heavy metal assay, arsenic, uranium, antimony, beryllium, cyanide, nickel, thallium, diquat, endothall, glyphosate, dioxin, phosphorus, phosphates, sodium carbonate, sodium bicarbonate, potassium bicarbonate, calcium carbonate, calcium-magnesium carbonate, potassium hydroxide, sodium hydroxide, phosphoric acid, acetic acid, citric acid, hydrochloric acid and sulfuric acid, residual disinfectants and disinfection byproducts, and chemical pesticides. On-site automated testing devices ample test results reports are logged into black water bottling process server including date of sampling, type of product sampled, unit package production code, and results of the analysis and reported to appropriate agencies.

The empty bottle filling station 2431 is supplied with a beverage mixture from a beverage mixing tank 2410 for filling the beverage mixture into the bottles in a predetermined volume. Predetermined amounts of ingredients are combined and mixed in the beverage mixing tank 2410. The ingredients can include predetermined quantities of deionized purified water 2400 from a tank, and fulvic acid 2491, and humic acid 2492 additives. Alcoholic beverages can include ingredients including ulmic acid 2494 in alcohol 2495. Ulmic acid 2494 is a fraction of humic acid that is soluble in alcohol 2495. The beverage mixture can also include in predetermined quantities flavorings 2423, additives 2424, vitamins 2425, minerals 2426, carbonation 2427, one or more artificial sweetener 2428, and one or more natural sweetener 2429. The total predetermined quantities of the ingredients are deposited into the beverage mixing tank 2410 and blended into the final product mixture.

After the bottles are filled at the empty bottle filling station 2431 they are conveyed to a bottle capping station 2432 where a cap is coupled to the filled bottle. A bottle volume sensor station 2434 then is used to confirm the predetermined volume has been filled into the bottle. A bottle labeling station 2436 then affixes a label to the bottle. In some instances the bottle or beverage container may be pre-printed with the labeling information including the product name, contents information and other desired and required information.

The bottles are conveyed to a bottle quality control station 2440 where one or more inspector and/or automated sensors including scanners, photographic image recognition devices, digital scales and other quality control evaluation test devices can perform quality control inspections to ensure the quality of the bottling processes. The bottles that pass the bottle quality control station 2440 evaluations are then conveyed to a bottle packing station 2450. During the process of filling, capping or sealing either single-service or multiservice containers, the performance of the filler, capper or sealer shall be monitored and the filled containers visually or electronically inspected using the automated sensors including scanners, photographic image recognition devices, digital scales and other quality control evaluation test devices to assure they are sound, properly capped or sealed, and coded and labeled. Containers that do not pass inspection shall be reprocessed or rejected and not sent to packaging. Bottling electronic monitoring includes bottle quality control devices configured for using automated sensors including scanners, photographic image recognition devices, digital scales and other quality control evaluation test devices to assure bottles and containers are sound, properly capped or sealed, coded and labeled and to physically remove bottles and containers that do not pass inspections of one embodiment.

All containers, caps and closures shall be sampled and inspected to ascertain that they are free from microbial organisms and other forms of contamination. Testing for bacteriological contamination shall be performed using approved methods including a bacteriological swab and/or rinse count at least once each 3 months. Testing for bacteriological contamination shall be conducted on not less than four containers, caps and closures selected just prior to filling and sealing. No more than twenty-five percent of the samples may exceed more than one bacteria per milliliter of capacity or one colony per square centimeter of surface area. All samples shall be free of coliform organisms. The procedure and apparatus for these bacteriological tests shall be in conformance with those recognized by the government agency or agencies having jurisdiction. Tests shall be performed either by qualified plant personnel or a competent commercial laboratory.

Predetermined packaging for each beverage type and beverage container is positioned at a bottle packing receiving station 2452. All packaging materials shall be imprinted with a unit package production code. Each unit package from a batch or segment of a continuous production run of bottled drinking water shall be identified by a unit package production code. Imprinting of the unit package production code shall be uniquely codes with unit package production code data including the kind of product, volume produced, date produced, lot code used, and the distribution identification of the finished product to wholesale and retail outlets just prior to packaging of a product. The black water bottling process server shall produce an alphanumeric code and graphic barcode for each finished product batch for each different beverage container type and size. The alphanumeric code and graphic barcode will include codes to distinguish the unit package production code from other batches. The unit package production code shall identify a particular batch or segment of a continuous production run and the day produced. The plant shall record and maintain information as to the kind of product, volume produced, date produced, lot code used, and the distribution of the finished product to wholesale and retail outlets.

Predetermined packaging can include a non-corrosive and non-toxic disinfectant agent impregnated into the packaging materials including for example cardboard and plastic rings to prevent growth of bacteria and microorganisms on the beverage containers after packaging and during shipping. A bottle packing folding station 2454 uses the received predetermined packing materials and processes the materials for receiving a predetermined number of bottles. This may include for example folding of packing cartons, drink holders, loading plastic six-pack rings in an application device and other predetermined packing materials preparations. A bottle carton conveyer 2456 is used to convey folded cartons to an unloaded carton staging area 2458. The unloaded carton staging area 2458 is used for a carton assembly station 2460 for packing the cartons with bottles. An assembled cartons shipping conveyor 2474 is used for grouping and positioning assembled cartons for pick-up for delivery to a shipping area. The above has described an overview of a humic and fulvic black water based beverage for human consumption bottling apparatuses and processes 2490 of one embodiment.

Hot Fill:

The bottle filling process includes at least one sterilization process. The at least one sterilization process includes a hot fill process. The hot fill apparatus includes heating elements along the metal fill piping. The beverage containers are moved along the conveyor to an adjustable platform. The adjustable platform is automatically adjusted up or down to a fill height determined by a laser sensor that detects the top of the container. A digitally controlled valve of the heated metal fill piping is opened and closed using a signal from the bamboo leaf extraction network computer to dispense a predetermined volume of the heated mixed liquid that will fill the container to a predetermined volume below the top of the container.

The hot fill process heats the mixed liquids between 194 and 203 degrees Fahrenheit to ensure sterilization. These heat-up process temperatures can be used with glass and certain types of plastic containers that do not change form at these temperatures. The containers are filled with the heated mixed liquids including non-carbonated beverage and liquid food products such as fruit and vegetable juices, soft drinks, water and teas. The containers are hermetically sealed after filling to preserve the sterilization. The hermetically sealed containers are immediately cooled preserving the product and taste. The hot filling process eliminates the need of preservatives and chemicals while maintaining the same level of shelf life and nutritional properties of the beverage.

Cold Fill:

The at least one sterilization process includes in another embodiment a cold fill process. The cold fill process pressurizes the container by cooling the product then the cold product is added to the cold container. The cold fill process requires sterilization, which can be either a wet or dry sterilization. The cold fill process includes at least one of three cold fill technologies.

A first cold fill technology is Iso-barometric Fillers: Applied to carbonated soft drinks, where the packaging, in PET plastic or glass is filled in iso-barometric fillers, capped and pasteurized in an Iso-barometric tunnel. Filling is made at 3° C. to 4° C. temperatures.

A second cold fill technology is Ultra Clean Systems: applied to beverages filling at low temperatures, and where the environmental conditions are very strict. This type of cold fill process is used for products with a short expiring date of about 30 days- and are distributed at low temperature under chilled conditions. The products have high quality, and are flash pasteurized and including a flash pasteurized application to the carton and PET packaging.

A third cold fill technology is Steril filling: Sterile filling preserves the product best according to nutritional, organoleptic and shelf life qualities. Sterile filling processing sterilized the container before filling in a sterile environment, sterilizing the container with peroxide or per-acetic acid, then dried to eliminate any traces of it. The sterility of the filling atmosphere is achieved via air filtering and high temperature sterilization. Sterile filling can be used for carton packaging containers and PET bottles.

Aseptic Fill:

The at least one sterilization process includes in another embodiment Aseptic fill. The aseptic filling process flash pasteurizes the mixed product including the mixed liquid is heated to a temperature between 180° F.-220° F. for a few minutes then cooled and filled at room temperature. Aseptic processing is a process by which a sterile product including at least a food or pharmaceutical, is packaged in a container. Aseptic fill is appropriate for high acid products and the products can last up to 18 months and is great for dairy and beverages in glass, aluminum, or PET.

Mixing Tanks:

Mixing tanks, sometimes called Blending tanks can include single direction rotating paddles, counter-rotating paddles, multi-speed rotating dual blades and combination homogenizing mixing tanks.

Filtration:

Filtration is integrated along the flow lines of the liquids at every point where the liquid is being conveyed from one vessel to another. For example when a liquid is pumped from a storage tank to the mixing tank a series of filters of various mesh sizes are incorporated into the piping lines. At least one filter in the series of mesh sizes is 0.2 microns to capture bacteria. Multiple filtration assures clean clear beverages.

Figure 25:
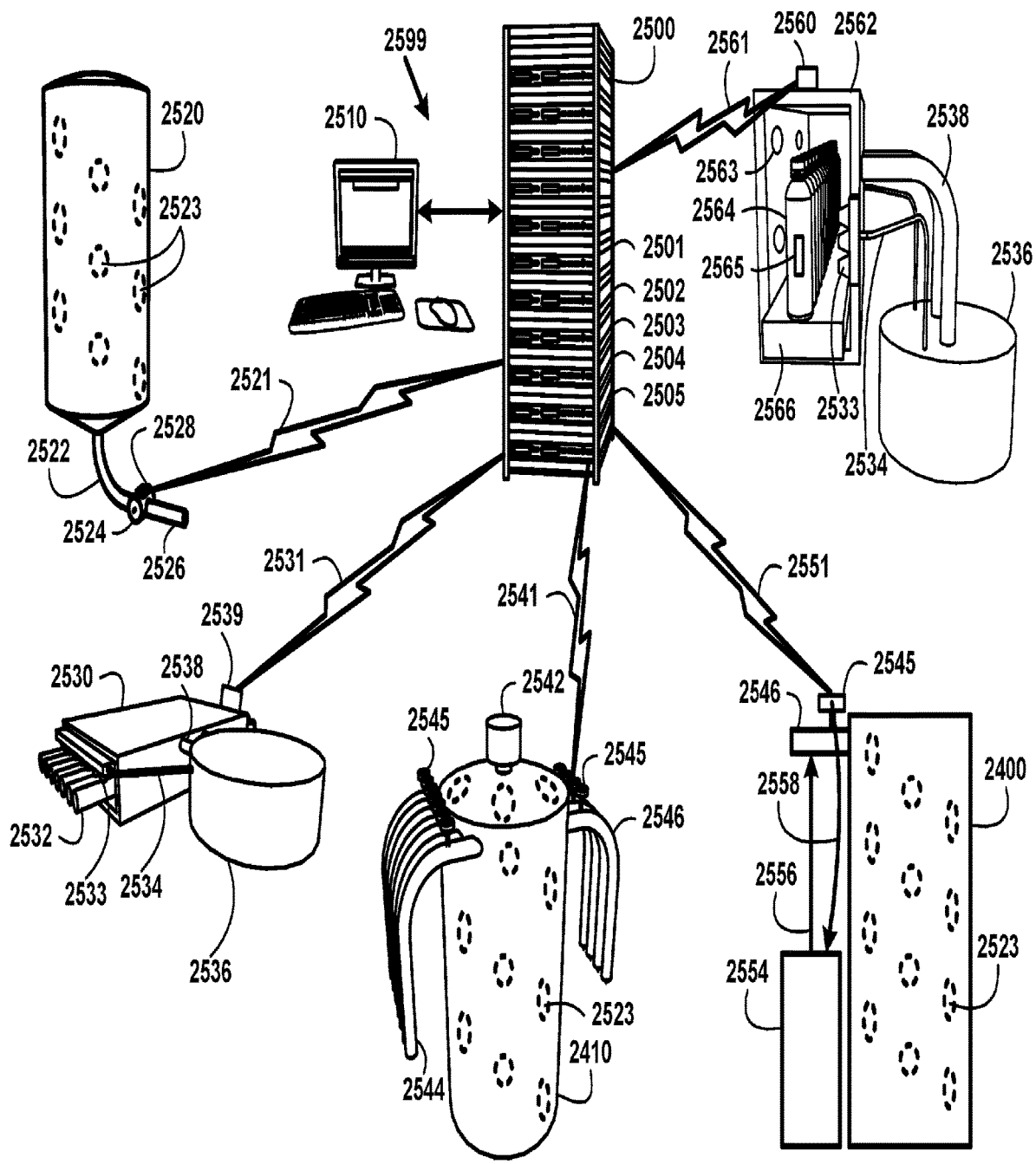
FIG. 25 shows for illustrative purposes only an example of a bottling electronic monitoring and control network of one embodiment.

Computer Controlled Monitoring and Processes:

FIG. 25 shows for illustrative purposes only an example of a bottling electronic monitoring and control network of one embodiment. FIG. 25 shows a humic and fulvic black water based beverage for human consumption bottling electronic monitoring and control network 2599 used for monitoring and controlling a bottling operation. The bottling electronic monitoring and control network 2599 includes at least one digital server 2500, at least one digital processor 2501, at least one digital memory device 2502, at least one Wi-Fi device 2503, at least one database 2504, at least one processing algorithm 2505, and at least one user computer 2510. The at least one digital server 2500 controls the bottling processes using data and parameters inputted by a user with the at least one user computer 2510 of one embodiment.

User inputted data and additional data is stored in the at least one digital memory device 2502 and at least one database 2504 creating a reference file for each beverage. The data includes predetermined quantities of each additive ingredient for each beverage to be formulated, a predetermined pH level range for each beverage, a predetermined temperature range, a bottle or beverage container size for a particular packaging mode, labeling information, and detailed information for each additive ingredient including pH level, calories per unit, a sweetness and taste indicator value, and other additive specific data. The at least one processing algorithm 2505 includes a formulation process to determine for example a projected pH level based on a combination of specific quantities of additive ingredients. The at least one digital processor 2501 is used to calculate the projected pH level based on the volumetric contributions of each additive ingredient of one embodiment.

Additional data is communicated to the at least one digital server 2500 using WI-FI communications and data signals from monitoring sensors at various points in the processing. In one embodiment for example, during each process, sensors and tracking devices are connected to each device that processes, mixes, sterilizes, and other operations of the bottles, beverage additive ingredients and bottles to ensure the beginning, intermediate and final processes are controlled to allow the final product to all safety and regulatory standards for human consumption and a desired product quality of one embodiment.

In addition a RFID, Bluetooth, NFC, sensors and tracking devices are coupled to the beverage containers 2565 of a beverage product to track the beverage distribution and track the consumption of the beverage product and disposal of the bottle container. A mobile device application is wirelessly coupled to the sensors and devices to allow a user to remotely monitor and observe the distribution, consumption, and disposal of the beverage of one embodiment.

An additive supply tank 2520 is equipped to receive an additive quantity control signal 2521 from the at least one digital server 2500. The signal is received using a predetermined quantity digital meter and monitor controller transceiver 2528. The additive supply tank 2520 includes a plurality of interior facing waterproof ultraviolet light sanitization fixtures 2523 to prevent bacterial growth and kill any microorganisms that may be present in the additive material prior to being conveyed to the mixing tank 2410. Coupled to additive bulk supply piping 2522 a metered supply pump 2524 opens a digitally controlled valve to allow the predetermined quantity to flow to the beverage mixing tank 2410 through metered supply piping 2526 of one embodiment.

A metered additive temperature control apparatus 2530 can receive a metered additive temperature control signal 2531 from the at least one digital server 2500 using a predetermined digital temperature controller transceiver 2539. Metered additive supply piping 2532 is equipped with a digital temperature meter 2533. The digital temperature meter 2533 measures the temperature of the additive flow.

The digital temperature meter 2533 transmits digital instructions through the digital temperature meter thermostat cabling 2534 to start the operation of a metered additive supply temperature adjusting apparatus 2536 should the additive flow temperature fall below or above a range determined by a predetermined temperature transmitted by the metered additive temperature control signal 2531. The predetermined temperature is set to a range for each specific additive to prevent growth of bacteria in the additive. The metered additive supply temperature adjusting apparatus 2536 can operate in a mode to either raise or lower the temperature using a reversible flow of a media in temperature control media piping 2538 to extract or add heat to adjust the additive flow temperature of one embodiment.

The beverage mixing tank 2410 includes a beverage mixing tank mixer motor 2542. The beverage mixing tank 2410 includes a plurality of interior facing waterproof ultraviolet light sanitization fixtures 2523 to prevent bacterial growth and kill any microorganisms that may be present in the additive material prior to being conveyed to the mixing tank 2410. An additive ingredient mixing tank control signal 2541 is received by the beverage mixing tank 2410 using a plurality of pH metering probe and digital transceiver 2545 coupled to each metered additive supply piping 2544. At least one pH metering probe and digital transceiver 2545 is coupled to de-ionized purified water supply piping 2546. The pH metering probe and digital transceiver 2545 measures the actual pH level of the additive ingredient as it flows into the beverage mixing tank 2410. The actual pH levels are transmitted to the at least one digital server 2500. This actual data is processed by the at least one processing algorithm 2505 using the at least one digital processor 2501 to determine any pH level adjustment in the combined ingredients of one embodiment.

The de-ionized purified water supply tank 2400 can receive a de-ionized purified water supply control signal 2551 from the at least one digital server 2500 using the pH metering probe and digital transceiver 2545. The de-ionized purified water supply control signal 2551 can include a final pH level adjustment instruction. The final pH level adjustment instruction is transmitted to a soda ash (NaOH) solution injector apparatus 2554 using pH metering probe and digital transmitter signal cabling 2558. The soda ash (NaOH) solution injector apparatus 2554 can inject into de-ionized purified water supply piping 2546 a predetermined pH level adjustment dose of soda ash to make the adjustment inject that quantity using NaOH injection piping 2556. The de-ionized purified water supply tank 2400 includes a plurality of interior facing waterproof ultraviolet light sanitization fixtures 2523 to prevent bacterial growth and kill any microorganisms that may be present in the de-ionized purified water prior to being conveyed to the mixing tank 2410 of one embodiment.

A bottling conveyor temperature control apparatus 2562 is used to control the temperature of the final beverage product after bottling. The bottling conveyor temperature control apparatus 2562 surround a section of a bottle conveyor 2566 with bottles on a conveyor 2564. The section of a bottle conveyer 2566 with the bottling conveyor temperature control apparatus 2562 includes in the surrounding structure a plurality of interior facing ultraviolet light fixtures 2563 to prevent bacterial growth and kill any microorganisms that may be present on the exterior of the bottles and caps while being conveyed to the bottle packing station 2450 of FIG. 24.

A bottling conveyor temperature controller transceiver 2560 can receive a bottling conveyor temperature control signal 2561 with a predetermined temperature. The digital temperature meter 2533 can signal using digital temperature meter thermostat cabling 2534 the metered additive supply temperature adjusting apparatus 2536 to extract or add heat using reversible flow of a media in the temperature control media piping 2538 of one embodiment. The bottling electronic monitoring and control network 2599 is used for metering, monitoring and controlling combining ingredient quantities, regulating ingredient and mixture temperature and PH level of the mixture of one embodiment.

Figure 26:
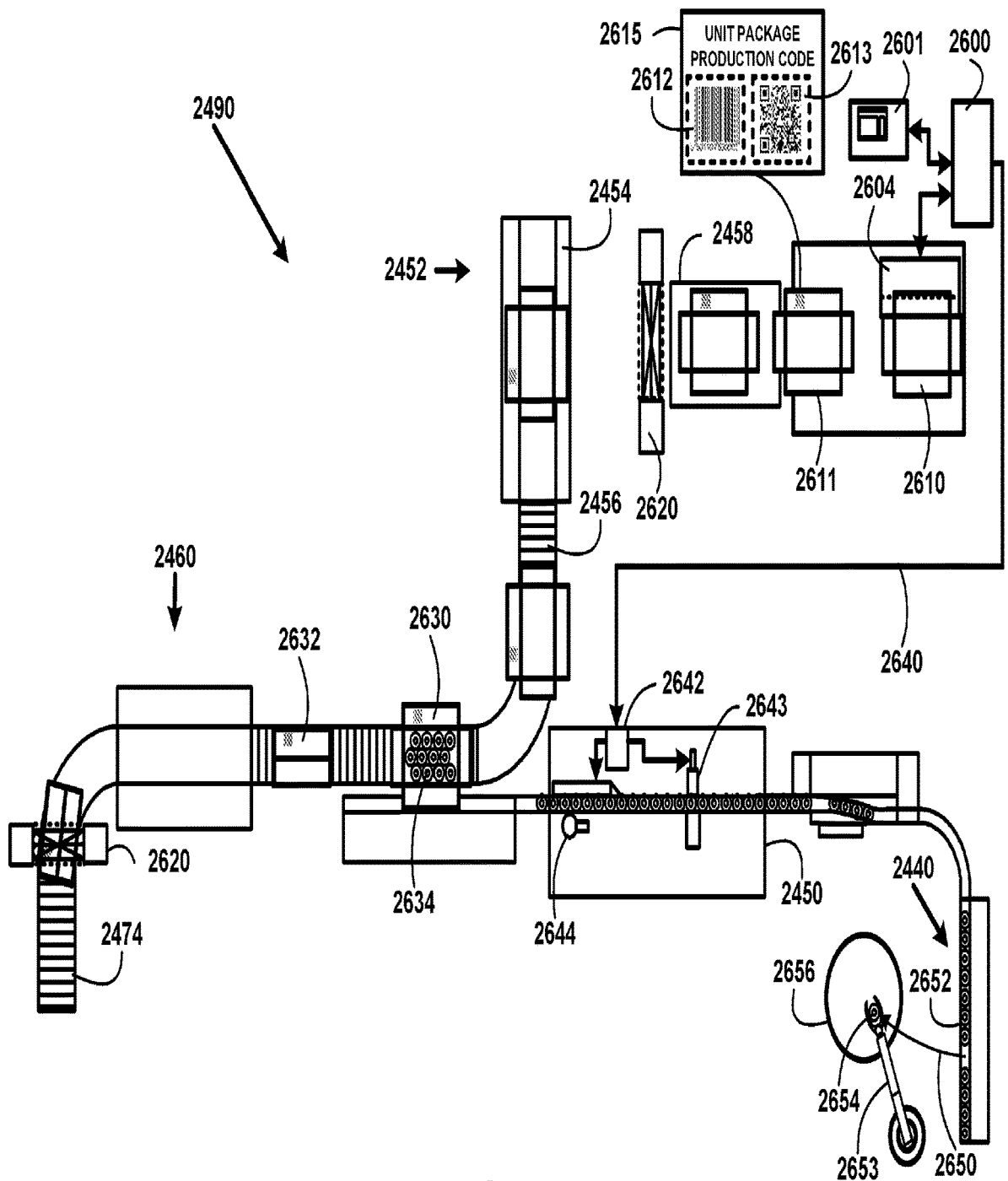
FIG. 26 shows for illustrative purposes only an example of a black water bottling quality control process of one embodiment.

Bottling Quality Control Process:

FIG. 26 shows for illustrative purposes only an example of a black water bottling quality control process of one embodiment. FIG. 26 shows a black water bottling quality control process including the bottle quality control station 2440. Bottling quality control includes a bottling facility physical plant, sanitation inspection procedures and processes including labeling and packaging. The black water beverage method and system bottling apparatuses and processes 2490 includes a black water bottling process server 2600 and computer 2601 to control and regulate black water bottling quality control processes of one embodiment.

The bottle quality control station 2440 processes filled, capped, and sealed bottles 2650 for inspections. Qualified personnel conduct physical inspections. Not shown are automated electronic and mechanical sensors and testing devices to inspect for contamination, improper capping and sealing. Inspection results are logged into the black water bottling process server 2600 by physical inspectors using the computer 2601. Automated electronic and mechanical sensors and testing devices transmit inspection results to the black water bottling process server 2600. Should a bottle not pass the inspection regimen physical inspectors are alerted by the black water bottling process server 2600 of an inspection rejected bottle 2654 for physically pulling inspection rejected bottle from the conveyor 2652 and transmitting a rejection signal to a robotic gripper 2653 for pulling inspection rejected bottle from the conveyor 2652 and depositing the inspection rejected bottle 2654 in a rejected bottle receptacle 2656 of one embodiment.

The bottle packing station 2450 is for receiving a unit package production code 2615 printing instructions 2640 for using a label printer 2642 apparatus and label application apparatus 2644 to affix a unit package production code 2615 includes a barcode 2612 and/or a QR code 2613 label to a bottle and for direct printing on a bottle surface 2643 the unit package production code 2615 data to inform consumers of ingredients, nutritional data and other information including a batch identifying code. The unit package production code 2615 barcode 2612 and/or QR code 2613 is read for example using an application on a users' smart phone of one embodiment.

Non-corrosive and non-toxic disinfectant agent impregnated flattened packaging 2610 materials are positioned for using a printer 2604 to print a unit package production code 2615. The unit package production code 2615 including a barcode 2612 and/or a QR code 2613 on the flattened packaging 2610 materials for providing automated identification of product batch data and packaged product tracking. Flattened packaging 2610 with a printed barcode 2611 passes through a barcode reader scanner 2620 with QR code reading capability to track the numbers of batch indicated product packaging used for a particular batch. The flattened packaging with a printed barcode 2611 is conveyed to the bottle packing receiving station 2452 for processing through the bottle packing folding station 2454. Folded bottle packing materials are set on the bottle carton conveyer 2456 for movement to the unloaded carton staging area 2458 of one embodiment.

The carton assembly station 2460 includes automated processes for robotic (not shown) placing of inspection approved filled, capped and sealed bottles in folded carton packaging. Folded packaging with bottles packed inside 2630 is processed to complete sealing of closed packaging 2632 with a plurality of labeled bottles 2634. Another barcode reader scanner 2620 registers a sealed closed package of bottles passing through on the assembled cartons shipping conveyor 2474 to identify and track the distribution of the batch identified product of one embodiment.

Figure 27:
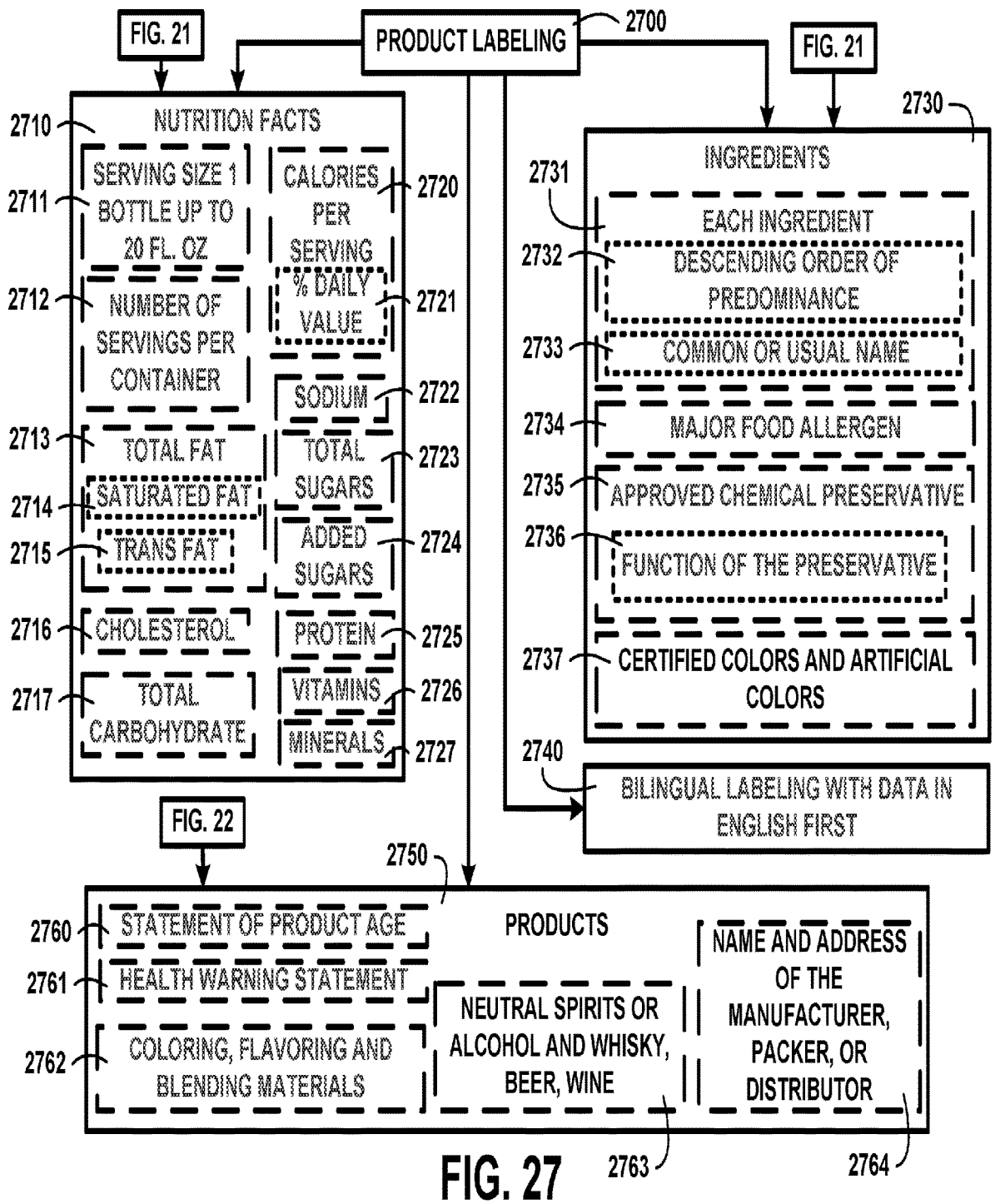
FIG. 27 shows a block diagram of an overview of product labeling of one embodiment.

Product Labeling:

FIG. 27 shows a block diagram of an overview of product labeling of one embodiment. FIG. 27 shows one embodiment of product labeling 2700. Nutritional data from FIG. 21 is transmitted using the black water bottling process server 2600 of FIG. 26 and computer 2601 of FIG. 26 for nutrients included in a product batch mixture. The black water bottling process server 2600 of FIG. 26 calculates volumes of the nutrients in a batch mixture for inclusion in nutrition facts 2710 data to be included in a product batch label. The nutrition facts 2710 data can include for example a serving size 1 bottle up to 20 fl. oz. 2711, number of servings per container 2712, total fat 2713 including saturated fat 2714 and trans fat 2715, cholesterol 2716, total carbohydrate 2717, calories per serving 2720, a % daily value 2721 calculated using the black water bottling process server 2600 of FIG. 26, sodium 2722, total sugars 2723 including added sugars 2724, protein 2725, vitamins 2726 and minerals 2727 of one embodiment.

The black water bottling process server 2600 of FIG. 26 can transmit from FIG. 21 ingredients 2730 included in a product batch mixture. Each ingredient 2731 is listed in a descending order of predominance 2732 using the calculated volumes from the black water bottling process server 2600 of FIG. 26 calculated volumes sorted by a descending order of predominance 2732. The ingredients can for example include a common or usual name 2733, the presence of any known major food allergen 2734, an approved chemical preservative 2735 including a function of the preservative 2736, and certified colors and artificial colors 2737. The black water bottling process server 2600 of FIG. 26 can using language databases translate the ingredients, nutrients and other batch mixture data in a desired foreign language to create bilingual labeling with data in English first 2740 of one embodiment.

Information from FIG. 22 for products 2750 is included in creating label data. Label data can include for example a statement of product age 2760 for example of an alcoholic beverage showing "Aged 5 years". Label data can include for example a health warning statement 2761, coloring, flavoring and blending materials 2762, type of alcohol neutral spirits or alcohol and whisky, beer, wine 2763 and name and address of the manufacturer, packer, or distributor 2764 of one embodiment.

The foregoing has described the principles, embodiments and modes of operation of the embodiments. However, the embodiments should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A black colored beverage, comprising:
 purified water safe for human consumption;
 humic acid and fulvic acid suspended within the purified water, wherein the suspended humic acid and fulvic acid are sufficiently concentrated and suspended within the water to imbue the purified water with a black color:
 at least one natural fruit flavoring mixed in the purified water with the suspended humic acid and fulvic acid; and
 a carbonation ingredient mixed in the mixture of at least one natural fruit flavoring, and purified water with the suspended humic acid and fulvic acid mixture.

2. The black colored beverage of claim 1, further comprising at least one vitamin additive mixed in the purified water.

3. The black colored beverage of claim 2, further comprising at least one of an herbal flavoring, a tea flavoring or a coffee flavoring mixed in the purified water to adjust the beverage taste.

4. The black colored beverage of claim 1, further comprising at least one mineral additive mixed in the purified water.

5. The black colored beverage of claim 1, further comprising a soda ash solution additive mixed in the purified water to adjust a pH level.

6. The black colored beverage of claim 1, further comprising at least one vitamin mixed in the purified water, wherein the at least one vitamin includes at least one of vitamin A, vitamin B complex, vitamin B6, vitamin B12, vitamin C, vitamin D, vitamin E, or vitamin K.

7. The black colored beverage of claim 1, wherein the at least one additive mixed in the purified water, wherein the at least one additive is at least one of a dietary supplement, *ginseng*, caffeine, an antioxidant, or an aloe extract ingredient.

8. A black colored beverage, comprising:
purified water safe for human consumption, wherein the purified water is purified with reverse osmosis;
humic acid and fulvic acid suspended within the purified water, wherein the suspended humic acid and fulvic acid are sufficiently concentrated and suspended within the water to imbue the purified water with a black color:
at least one nutritional additive mixed in the purified water having the suspended humic acid and fulvic acid, wherein the at least one nutritional additive comprises at least one of a group of at least a vitamin, a dietary supplement, a mineral, or a pH adjusting solution to add nutritional value;
at least one natural fruit flavoring mixed in the purified water having the suspended humic acid and fulvic acid and at least one nutritional additive; and
a carbonation ingredient mixed in the mixture of at least one natural fruit flavoring and purified water with the suspended humic acid and fulvic acid solution and the at least one nutritional additive.

9. The black colored beverage of claim 8, wherein the purified water has a total dissolved salt concentration <200 ppm.

10. The black colored beverage of claim 8, further comprising at least one nutritional additive and a soda ash solution.

11. The black colored beverage of claim 8, further comprising at least one of a group consisting of an herbal flavoring, a tea flavoring, or a coffee flavoring to add taste to the beverage.

12. The black colored beverage of claim 8, wherein the at least one nutritional additive mixed in the purified water comprises at least one of vitamin A, vitamin B complex, vitamin B6, vitamin B12, vitamin C, vitamin D, vitamin E, or vitamin K to add nutritional value to the beverage.

13. The black colored beverage of claim 8, wherein the at least one nutritional additive comprises at least one trace element, or an electrolyte.

14. The black colored beverage of claim 8, further comprising caffeine mixed in the purified water and wherein the at least one additive comprises vitamin C.

* * * * *